US011307146B2

(12) United States Patent
Willson et al.

(10) Patent No.: US 11,307,146 B2
(45) Date of Patent: Apr. 19, 2022

(54) SYSTEMS AND METHODS FOR DETECTION OF CHEMTILUMINESCENT REACTIONS

(71) Applicants: University of Houston System, Houston, TX (US); Instituto Tecnológico y de Estudios Superiores de Monterrey, Monterrey (MX)

(72) Inventors: Richard C. Willson, Houston, TX (US); Jinsu Kim, Houston, TX (US); Binh V. Vu, Houston, TX (US); Olga Patricia Vázquez Villegas, Monterrey (MX); Federico Augusto Ruiz Ruiz, Monterrey (MX); Marco Antonio Rito Palomares, Monterrey (MX)

(73) Assignees: University of Houston System, Houston, TX (US); Instituto Tecnológico y de Estudios Superiores de Monterrey, Monterrey (MX)

( * ) Notice: Subject to any disclaimer, the term of this patent is extended or adjusted under 35 U.S.C. 154(b) by 571 days.

(21) Appl. No.: 15/661,696

(22) Filed: Jul. 27, 2017

(65) Prior Publication Data

US 2018/0031484 A1 Feb. 1, 2018

Related U.S. Application Data

(60) Provisional application No. 62/368,516, filed on Jul. 29, 2016.

(51) Int. Cl.
| | |
|---|---|
| *G01N 21/76* | (2006.01) |
| *C12Q 1/26* | (2006.01) |
| *G01N 33/62* | (2006.01) |
| *G01N 33/66* | (2006.01) |
| *G01N 33/70* | (2006.01) |
| *G01N 21/75* | (2006.01) |

(52) U.S. Cl.
CPC .............. *G01N 21/76* (2013.01); *C12Q 1/26* (2013.01); *G01N 33/62* (2013.01); *G01N 33/66* (2013.01); *G01N 33/70* (2013.01); *G01N 2021/755* (2013.01); *G01N 2800/042* (2013.01)

(58) Field of Classification Search
CPC .............................................. G01N 2021/755
See application file for complete search history.

(56) References Cited

U.S. PATENT DOCUMENTS

| | | | | |
|---|---|---|---|---|
| 4,994,377 A | * | 2/1991 | Nakamura | C12Q 1/26 435/105 |
| 5,089,424 A | | 2/1992 | Khalil et al. | |
| 6,068,979 A | * | 5/2000 | Akhavan-Tafti | C12Q 1/28 435/6.11 |
| 2002/0123059 A1 | | 9/2002 | Ho | |
| 2003/0092194 A1 | | 5/2003 | Gambini et al. | |
| 2007/0264629 A1 | * | 11/2007 | Holmes | B01L 3/5027 435/5 |
| 2010/0075352 A1 | | 3/2010 | Umegae | |
| 2011/0165608 A1 | * | 7/2011 | Machida | G01N 33/70 435/28 |
| 2014/0273272 A1 | | 9/2014 | Gayda et al. | |

FOREIGN PATENT DOCUMENTS

WO WO2008072702 A1 12/2007

OTHER PUBLICATIONS

Daughters K. et al. "Salivary oxytocin concentrations in males following intrasanal administration of ocytoxin: A double-blind, cross-over study." *PLOS ONE*; pp. 1-11, 2015.
Linhardt R.J. et al. "Separation and Purification of Carbohydrates." *Glycosci. Chem. Chem. Biol.*; pp. 63-74, 2002.
PCT International Search Report and Written Opinion issued in International Application No. PCT/US2017/044173 dated Oct. 19, 2017.
Young, R.A., The Precipitation of Carbohydrates by Neutral Salts, *J. Physiol.* 22; pp. 401-422, 1898.

* cited by examiner

*Primary Examiner* — Bin Shen

(74) *Attorney, Agent, or Firm* — Parker Highlander PLLC

(57) ABSTRACT

Methods, devices and kit for analyzing a sample comprising 1,5-anhydroglucitol and a first analyte via one or more chemiluminescent reactions. Certain embodiments include measuring a first light response resulting from a first chemiluminescent reaction and measuring a second light response resulting from a second chemiluminescent reaction. Certain embodiments also include comparing the first light response to the second light response to determine a ratio of 1,5-anhydroglucitol and the first analyte.

14 Claims, 32 Drawing Sheets

(a) LabView print panel (a) LabView block diagram (a) PMT with 10 µg/mL HRP-Streptavidin        (b) PMT with 1 µg/mL HRP-Streptavidin

SYSTEMS AND METHODS FOR DETECTION OF CHEMTILUMINESCENT REACTIONS

CROSS-REFERENCE TO RELATED APPLICATIONS

This application claims priority to U.S. Provisional Patent Application Ser. No. 62/368,516 filed Jul. 29, 2016, the entire contents of which are incorporated herein by reference.

TECHNICAL FIELD

Exemplary embodiments of the present disclosure relate to systems, methods and kits for analyzing a body fluid sample. Particular embodiments relate to luminescence-based assay and point-of-care (POC) photon detection for determining low level analytes in body fluid, as a noninvasive screening method. In an assay format, an analyte of interest is treated with reagents in light generating reactions to produce photons as output signal. The emitted photons are detected using with POC detector device that can be controlled and monitored via devices with computing and displaying capability, including for example, mobile devices such as smart phone.

BACKGROUND INFORMATION

Early diagnosis of type 2 diabetes (T2D) is paramount important to reduce the complications of diabetes. For the glycemic monitoring in T2D, one can measure metabolites, such as 1,5-anhydroglucitol (1,5-AHG), HbA1c and glucose in blood samples. Recent report has revealed a strong association of T2D with 1,5-AHG in saliva as a noninvasive marker, resulting in benefit of patients who are adverse to blood sampling. 1,5-AHG is an unmetabolizable glucose analogue which is present in human blood due predominantly to dietary ingestion. In physiology, the 1,5-AHG level is balanced by being reabsorbed and excreted through kidney and urine, respectively. Normal range of 1,5-AHG level in human body is around 6.8-32.3 µg/ml for people in US. 1,5-AHG concentration in blood decreases during times of hyperglycemia, since reabsorption is completely inhibited by glucose at fructose and mannose active transporter; Therefore, monitoring 1,5-AHG in saliva is useful in achieving glycemic control.

To determine the concentration of 1,5-AHG, conventional methods such as liquid chromatography, gas-liquid chromatography and HPLC can be used. However, these methods require a large amount of sample volume, a series of sample preparation, complex laboratory equipment and trained personnel. An alternative to the conventional methods is to use enzymatic systems. Pyranose oxidase (PROD) has been used for determining D-glucose and 1,5-AHG in clinical analysis. PROD oxidizes the second position hydroxyl group of 1,5-AHG and generates hydrogen peroxide which can be detected using a variety of methods, including colorimetry, electrochemical and chemiluminescent assay. Therefore, 1,5-AHG is indirectly determined by measuring the generated hydrogen peroxide as shown in reaction 2 of FIG. 1 section (b). However, saliva sample contains D-glucose, which is also oxidized by PROD and produces hydrogen peroxide, thus, interferes with 1,5-AHG measurement. In this case, pretreatment of the sample is required to keep D-glucose from reaction with PROD as shown reaction 1 of FIG. 1 section (a).

As such, a need currently exists for an improved technique for detecting analytes such as 1,5-AHG in body fluid samples.

SUMMARY

Exemplary embodiments of the present disclosure relate to systems, methods and kits for measuring an analyte, including for example, 1,5-anhydroglucitol, in a body fluid sample.

Certain embodiments include a method for analyzing a sample, where the method comprises: obtaining a sample comprising 1,5-anhydroglucitol and a first analyte; adding a first reagent to the sample, wherein the first reagent causes a first chemiluminescent reaction with the sample; measuring a first light response resulting from the first chemiluminescent reaction; and adding a second reagent to the sample. In particular embodiments, the second reagent is sequentially added to the sample after the first reagent is added to the sample; and the second reagent causes a second chemiluminescent reaction with the sample. Specific embodiments include measuring a second light response resulting from the second chemiluminescent reaction; and comparing the first light response to the second light response to determine a ratio of 1,5-anhydroglucitol and the first analyte.

In particular embodiments, the sample comprises saliva, urine, blood, and/or interstitial fluid. In some embodiments, the first analyte is glucose, L-sorbose, D-xylose, D-galactose, glucono-δ-lactone, urea, creatinine, or creatine. In specific embodiments, the first reagent is glucose oxidase and the second reagent is pyranose oxidase. In specific embodiments, measuring the first light response resulting from the first chemiluminescent reaction and the second light response resulting from the second chemiluminescent reaction comprises measuring photons with a light detector.

In certain embodiments, the light detector is selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, or smart watch camera. In particular embodiments, the first reagent and the second reagent are added to the sample via a microfluidic device. In some embodiments, comparing the first light response to the second light response to determine a ratio of 1,5-anhydroglucitol and the first analyte comprises transmitting data to a computer processor. Specific embodiments further comprise accessing a lookup table with the computer processor. In certain embodiments, the lookup table comprises an indication of a physiological condition. In particular embodiments, the physiological condition is related to an insulin level of a person from whom the sample was obtained. Some embodiments further comprise normalizing the ratio based on a measurement of a marker in the sample. In specific embodiments, the marker is urea, creatinine, creatine, human serum albumin, or hemoglobin. In certain embodiments, the sample comprises urine, blood or saliva.

Exemplary embodiments include a kit comprising a chamber configured to sequentially add a first reagent and a second reagent to a sample, where: the sample comprises a first analyte and a second analyte; the first reagent causes a first chemiluminescent reaction with the sample; and the second reagent causes a second chemiluminescent reaction with the sample. Exemplary embodiments also include a light detection device, where the light detection device is configured to be able to: measure first data correlating to a first light response resulting from the first chemiluminescent reaction; and measure second data correlating to a second light response resulting from the second chemiluminescent reaction. Exemplary embodiments also include a communication module configured to transmit the first data and the second data from the light detection device to a computer processor, where the computer processor is configured to calculate a ratio of the first analyte to the second analyte based on the first data and the second data.

In certain embodiments, the chamber comprises a wicking member configured to wick the sample. In particular embodiments, the first reagent is absorbed in a first portion of the wicking member and the second reagent is absorbed in a second portion of the wicking member. In some embodiments, the wicking member is configured to wick the sample to the first portion of the wicking member; and the wicking member is configured to wick the sample to the second portion of the wicking member. In specific embodiments, the wicking member is configured to wick the sample to the first portion prior to wicking the sample to the second portion. In certain embodiments, the first analyte is glucose. In particular embodiments, the second analyte is 1,5-anhydroglucitol. In some embodiments, the computer processor is contained within a wireless communication device. In specific embodiments, the wireless communication device is a cellular phone. In certain embodiments, the communication module is configured to wirelessly transmit data from the light detection device to the computer processor. In particular embodiments, the computer processor is configured to access a lookup table. In some embodiments, the lookup table comprises an indication of a physiological condition. In specific embodiments, the physiological condition is related to an insulin level of a person from whom the sample was obtained.

In certain embodiments, the sample comprises saliva, urine, blood and/or interstitial fluid. In particular embodiments, the first analyte is glucose, urea, creatinine, or creatine. In some embodiments, the first reagent is glucose oxidase. In specific embodiments, the second reagent is pyranose oxidase. In certain embodiments, the first data comprises a first measure of photons relating to the first chemiluminescent reaction; and the second data comprises a second measure of photons relating to the second chemiluminescent reaction. In particular embodiments, the light detection device is selected from the group consisting of a charged coupled device (CCD), avalanche diode, multipixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellphone camera, web camera, or smart watch camera. In some embodiments, the computer processor is configured to normalize the ratio based on a measurement of a marker in the sample. In specific embodiments, the marker is urea, creatinine, creatine, human serum albumin, or hemoglobin. In certain embodiments, the sample comprises urine, blood or saliva.

Exemplary embodiments of the present disclosure include chemiluminescence-based photon detectors for determining low level 1,5-AHG in body fluid in a mobile format, including for example, as a smart phone accessory. In one embodiment of the assay format, the inventors first oxidized 1,5-AHG in a sample solution with PROD to produce hydrogen peroxide, followed by adding 5-amino-2,3-dihydro-1,4-phthalaxinedione (luminol) and horseradish peroxidase (HRP). The emitted light from the luminol reaction as shown in FIG. 1(b) was detected using photon sensors, including the avalanche photodiode (APD) arrays or photomultiplier tube (PMT).

Particular embodiments relate to luminescence-based assay and point-of-care (POC) photon detection for determining low level analytes in body fluid, as a noninvasive screening method. In an assay format, an analyte of interest is treated with reagents in light generating reactions to produce photons as output signal. The emitted photons are detected using with POC detector device that can be controlled and monitored via devices with computing and displaying capability, including for example, mobile devices such as a smart phone.

In an embodiment, the analyte of interest is 1,5-anhydroglucitol, glucose, creatine, creatinine, urea, metabolites, a protein, a peptide, a hormone, a biomarker, a toxin, or a modified (e.g., phosphorylated or acetylated) protein.

In an embodiment, the specimen in which the analyte is to be detected comprises a biopsy specimen, blood, serum, plasma, stool, saliva, sputum, CSF, lavage fluid, nasal wash, urine, cell lysate, drinking water, natural water, sea water, soil water, soil leachate, fresh tissue, frozen tissue, neutral formalin-treated tissue, formalin fixed paraffin embedded tissue block, or an ethanol-fixed paraffin-embedded tissue block.

In accordance with an embodiment of this invention, a specimen is optionally pre-treated for concentration of the analyte, removal of particulates, contaminants, interferences, or reaction inhibitors, reduction of viscosity, improvement of handling properties, or to modify the analyte for improved detection.

In additional embodiment, the methods to selectively remove or modify the interferences or contaminants include the uses of antibody capturing, aptamer capturing, enzymatic reactions, chemical modifications or chromatography techniques such as ion exchange, HIC, metal chelate, boronate, or affinity.

In an embodiment, the readout method by which the analyte is detected is the emission of light by chemiluminescence, bioluminescence, or any method may be used for generate the light signal in the method of the present invention.

In an embodiment, the analyte is reacted to produce hydrogen peroxide thru enzymatic coupled reaction. Hydrogen peroxide is detected by chemiluminescent reaction with chemiluminescent substrate to produce light signal.

In an embodiment, the reagents used to generate light output are chemiluminescent substrates, such as luminol, isoluminol, 1,2-dioxetanes, peroxyoxalate compounds and dyes.

In an embodiment, the luminescent signal is generated by reaction of chemiluminescent substrate and hydrogen peroxide that is catalyzed by enzyme, such as horseradish peroxidase.

In another embodiment, the luminescent signal is generated by reaction of chemiluminescent substrate and hydrogen peroxide with metal nanoparticles, such as silver nanoparticles.

In an embodiment, the luminescent signal is obtained without enzyme by reacting luminol and hydrogen peroxide in the presence of a ferricyanide ion.

In an embodiment, the luminescent signal is obtained by reacting luminol and hydrogen peroxide in the presence of iron oxide nanoparticles.

In an embodiment, the luminescent signal is obtained by reacting luminol and hydrogen peroxide in the presence of silver catalyst.

In an embodiment, the luminescent signal is obtained by reacting lucigenin with hydrogen peroxide in the presence of a metal ion.

In an embodiment, the luminescent signal is obtained by reacting an aryl oxalate such as bis(2,4,6-trichlorophenyl) oxalate with hydrogen peroxide in the presence of a fluorescent substance.

In an embodiment, the assay is done on a microfluidic device which comprises of multiple functional aspects: separation or removal of interferences, reaction to generate signal, and optical signal readout areas. In additional embodiment, the microfluidic device contains multiple separation/removal, reaction, and signal readout areas for multiplexing, where more than one analyte can be assessed.

In an embodiment, the separation area in microfluidic device contains adsorbent or absorbent to separate or remove interferences from analytes.

In another embodiment, the separation area in microfluidic device contains enzyme to convert interferences to non-interferences.

In another embodiment, the interferences are enzymatically converted to hydrogen peroxide which reacts with chemiluminescent substrate to generate light signal. Interferences and hydrogen peroxide are consumed in the process and their signal, which is read by light detector, can be used for calibration. Subsequence steps then convert analyte to light signal and read out by light detector.

In an embodiment, the luminescent signal output is collected by collection optics and subsequently detected by light detector such as but not limit to, charged coupled device (CCD), avalanche diode, (multi-pixel photon counter) MPPC or silicon photomultiplier (SiPMT), charged coupled device (CCD) sensor, complementary metal-oxide-semiconductor (CMOS) sensor, scientific CMOS (sCMOS) sensor, photomultiplier tubes (PMT). The light detector can be function as a point-of-care device connected and controlled via wired or wireless connection by personal computer, laptop, tablet, smart phone, smart watch, or any similar devices with computing and displaying capabilities.

The details of one or more embodiments of the invention are set forth in the accompanying drawings and the description below.

Certain terminology is used in the following description are for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

Exemplary embodiments of the present disclosure are provided in the following drawings. The drawings are merely examples to illustrate the structure of exemplary devices and certain features that may be used singularly or in combination with other features. The invention should not be limited to the examples shown.

DETAILED DESCRIPTION

Figure 2:
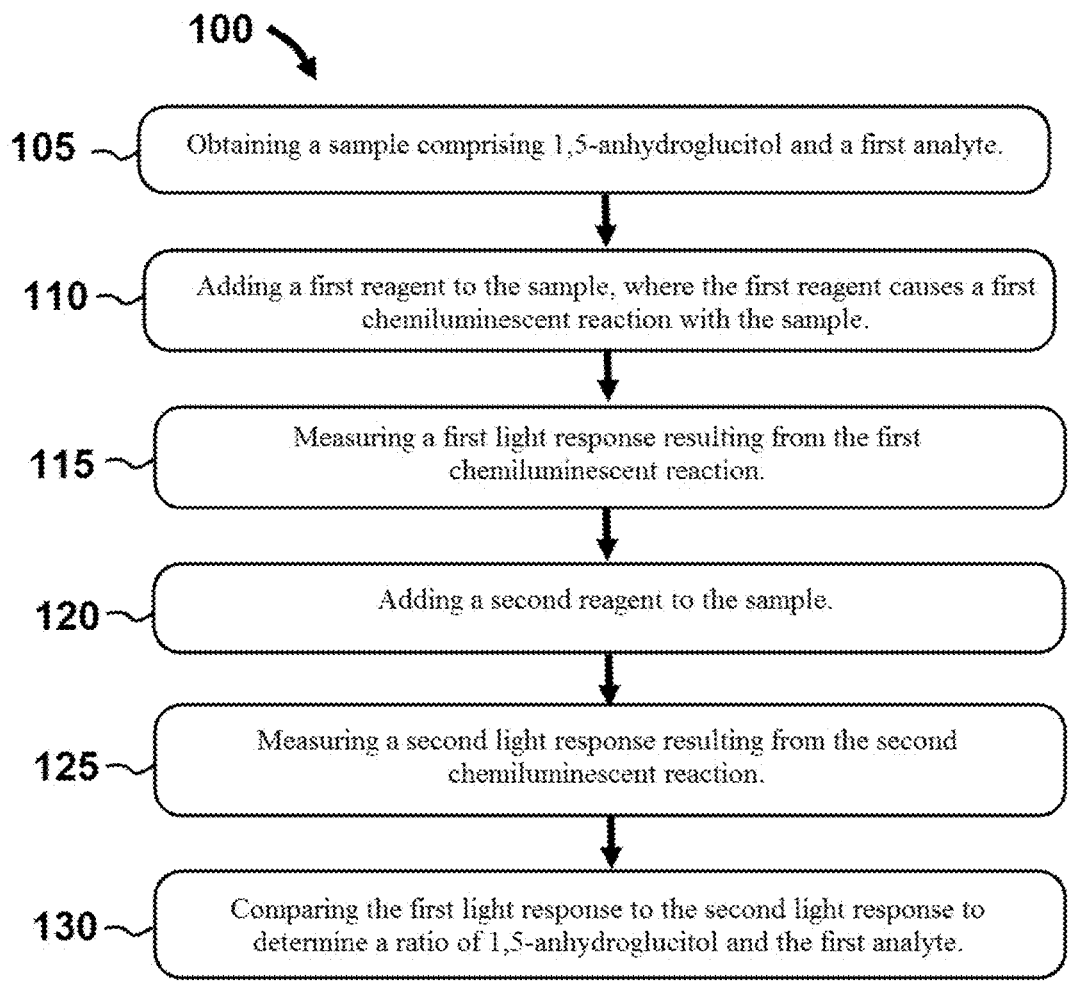
FIG. 2 illustrates a flowchart for a sample analyzing method.

An overview of exemplary embodiments will be presented initially, followed by more detailed discussion of particular features of the exemplary embodiments. Referring now to FIG. 2, a flowchart is presented for a sample analyzing method 100 comprising multiple steps. In certain embodiments, the sample may comprise a body fluid, including for example saliva or urine.

In this embodiment, method 100 includes a first step 105 comprises obtaining a sample comprising 1,5-anhydroglucitol and a first analyte. In particular embodiments, the analyte may be glucose, urea, creatinine, or creatine. Method 100 also comprises a step 110 comprising adding a first reagent to the sample, where the first reagent causes a first chemiluminescent reaction with the sample. In specific embodiments, the first reagent may be glucose oxidase.

In this embodiment, method 100 also comprises a step 115 of measuring a first light response resulting from the first chemiluminescent reaction and a step 120 of adding a second reagent to the sample. In particular embodiments, the second reagent may be pyranose oxidase and the first reagent and the second reagent can be added to the sample via a microfluidic device.

In the embodiment of FIG. 2, the second reagent can be sequentially added to the sample after the first reagent is added to the sample, where the second reagent causes a second chemiluminescent reaction with the sample.

Method 100 further comprises a step 125 of measuring a second light response resulting from the second chemiluminescent reaction. In particular embodiments, measuring the first light response resulting from the first chemiluminescent reaction and the second light response resulting from the second chemiluminescent reaction comprises measuring photons with a light detector. In specific embodiments, the light detector may be a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, or smart watch camera.

In addition, method 100 comprises a step 130 of comparing the first light response to the second light response to determine a ratio of 1,5-anhydroglucitol and the first analyte. In certain embodiments, comparing the first light response to the second light response to determine a ratio of 1,5-anhydroglucitol and the first analyte comprises transmitting data to a computer processor. In some embodiments, the lookup table may comprise an indication of a physiological condition, including for example, a physiological condition that is related to an insulin level of a person from whom the sample was obtained.

It is understood that other embodiments of the present disclosure may include additional or fewer steps than those shown in FIG. 2 and described above. Certain embodiments may also comprise kits configured to perform methods such as those described herein.

Figure 3:
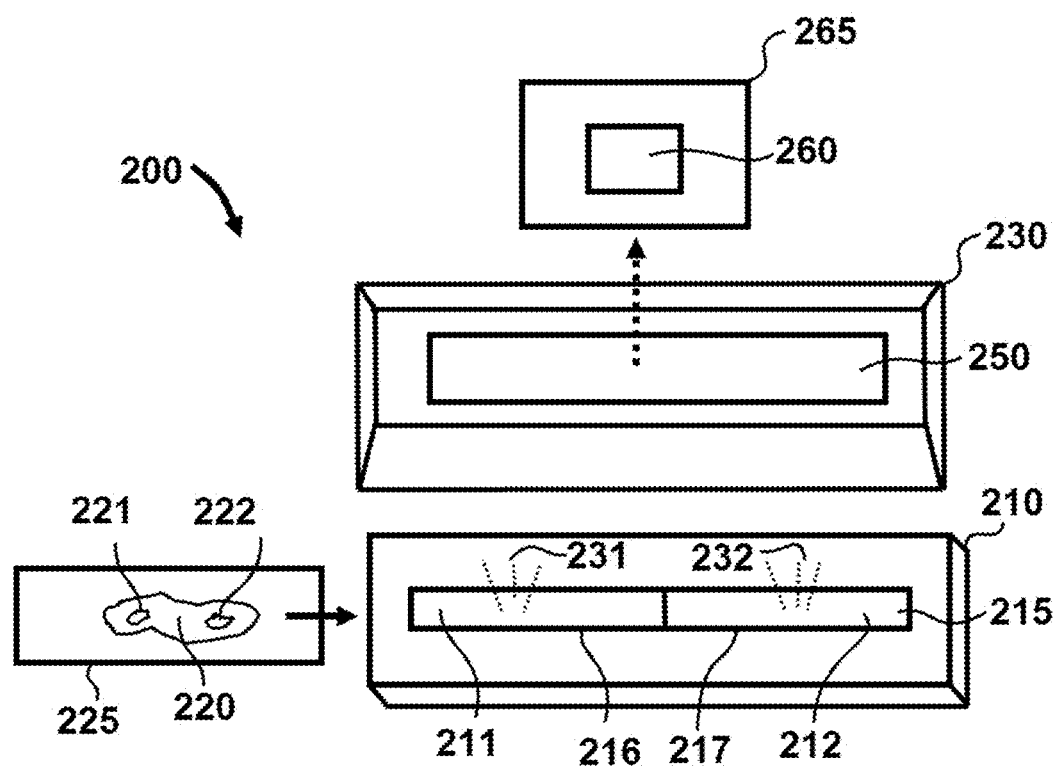
FIG. 3 illustrates a schematic of a kit comprising a chamber configured to sequentially add a first reagent and a second reagent to a sample.

Referring now to FIG. 3, certain embodiments include a kit 200 comprising a chamber 210 configured to sequentially add a first reagent 211 and a second reagent 212 to a sample 220. In the embodiment shown, sample 220 is placed on a cassette 225 that can be inserted in to chamber 210. In certain embodiments, sample 220 comprises a first analyte 221 and a second analyte 212.

In the embodiment shown, first reagent 211 and second reagent 212 can respectively cause a first chemiluminescent reaction (that produces a first light response 231) and a second chemiluminescent reaction (that produces a second light response 232) with sample 220. Kit 200 can further comprise a light detection device 230 that is configured to measure a first set of data correlating to first light response 231 resulting from the first chemiluminescent reaction. In addition, light detection device 230 can be configured to measure a second set of data correlating to second light response 232 resulting from the second chemiluminescent reaction.

Kit 200 can further comprise a communication module 250 configured to transmit the first data and the second data from light detection device 230 to a computer processor 260.

In particular embodiments, computer processor 260 can be configured to calculate a ratio of the first analyte to the second analyte based on the first data and the second data.

In certain embodiments, chamber 210 comprises a wicking member 215 configured to wick sample 220 such that first reagent 211 is absorbed in a first portion 216 of the wicking member 215 and second reagent 212 is absorbed in a second portion 217 of wicking member 215. In certain embodiments, wicking member 215 is configured to wick sample 220 the first portion 216 of wicking member 215 prior to wicking sample 220 to second portion 217. In particular embodiments, first analyte 221 may be 1,5-anhydroglucitol and second analyte 222 may be glucose.

Computer processor 260 may be contained within a wireless communication device 265, including for example, a cellular phone. In addition, communication module 250 can be configured to wirelessly transmit data from the light detection device 230 to computer processor 260.

In particular embodiments, computer processor 260 can be configured to access a lookup table that comprises an indication of one or more physiological conditions, including for example, those related to an insulin level of a person from whom sample 220 was obtained.

In certain embodiments, sample 220 may comprise a bodily fluid, including for example, saliva or urine. First analyte 221 may be glucose, urea, creatinine, or creatine, and first reagent 211 may be glucose oxidase in particular embodiments. In addition, second reagent may be pyranose oxidase in specific embodiments.

During operation of kit 200, data correlating to first light response 231 and second light response 232 may comprise a measure of photons relating to the first and second chemiluminescent reactions, respectively. In exemplary embodiments, light detection device 230 may include a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellphone camera, web camera, or smart watch camera.

It is understood that other embodiments of the present disclosure may comprise features or components different than those shown and described in the discussion of the figures.

Multi-Pixel Photon Counter (MPPC)

Certain embodiments of the present disclosure utilize a light detection device configured as a multi-pixel photon counter (MPPC), which is a solid state based detector referred to as a silicon photomultiplier (SiPM). The SiPM is a device comprising multiple avalanche photodiode (APD) arrays on a silicon substrate. Normally, an APD is operated with the reverse bias below breakdown voltage to convert light to electric current by photoelectric effect. However, in an SiPM, the APD array is operated above their breakdown voltage, in Geiger mode. Although the digital output type works in digital/switching mode, the SiPM is, in general, an analog output device, because all APD arrays are read in parallel, generating an integrated analog signal. The inventors used the MPPC (Hamamatsu, C12662-350, analog output type), detecting light in a dynamic range of $10^6$ to $10^{10}$ photons within 3 mm$^2$ area in which 3,600 APDs are arrayed.

Analog-to-Digital Converter (ADC)

Figure 4A:
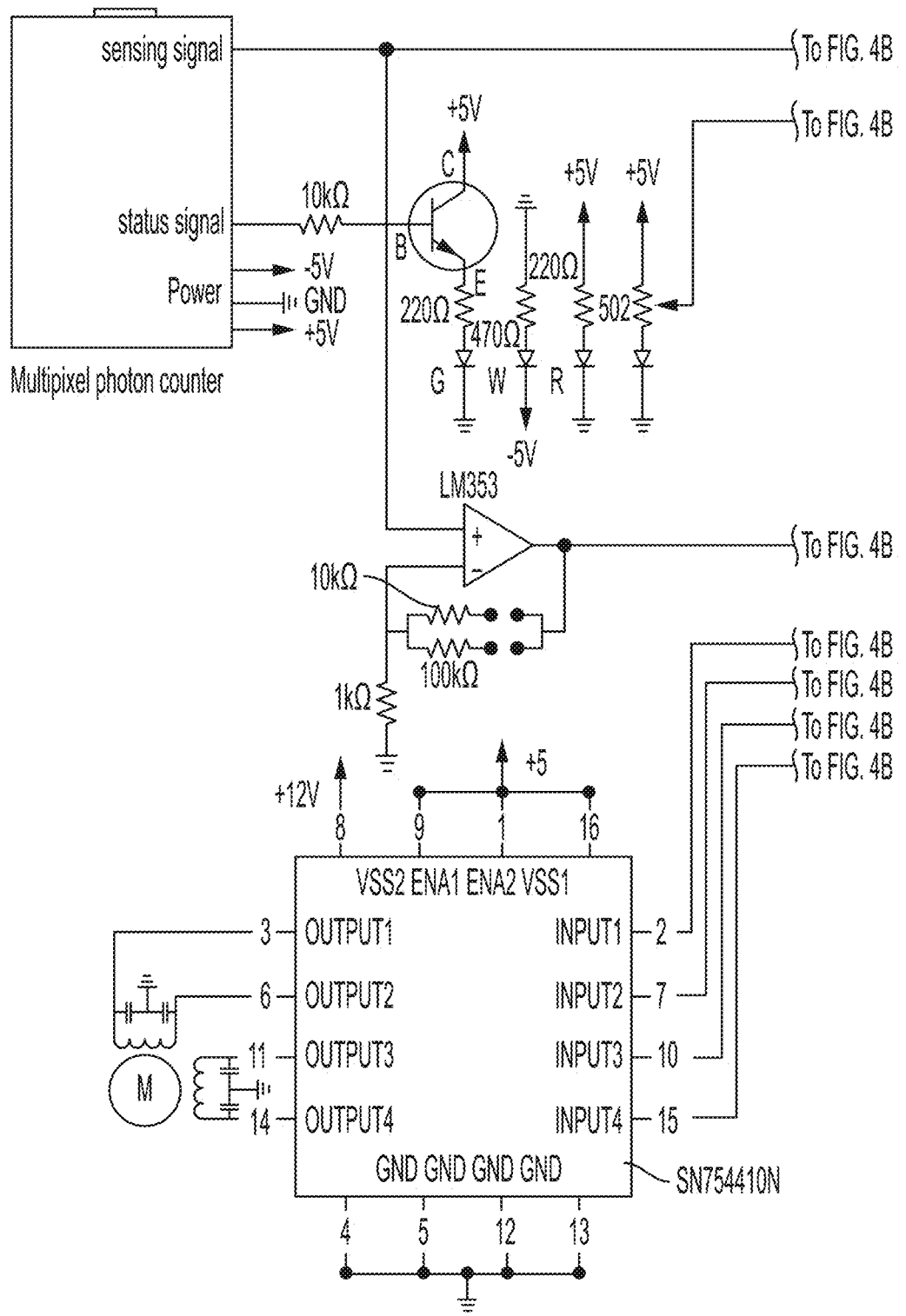
FIGS. 4A-C illustrate a schematic of a circuit diagram for ADC and stepper motor control.
Figure 4B:
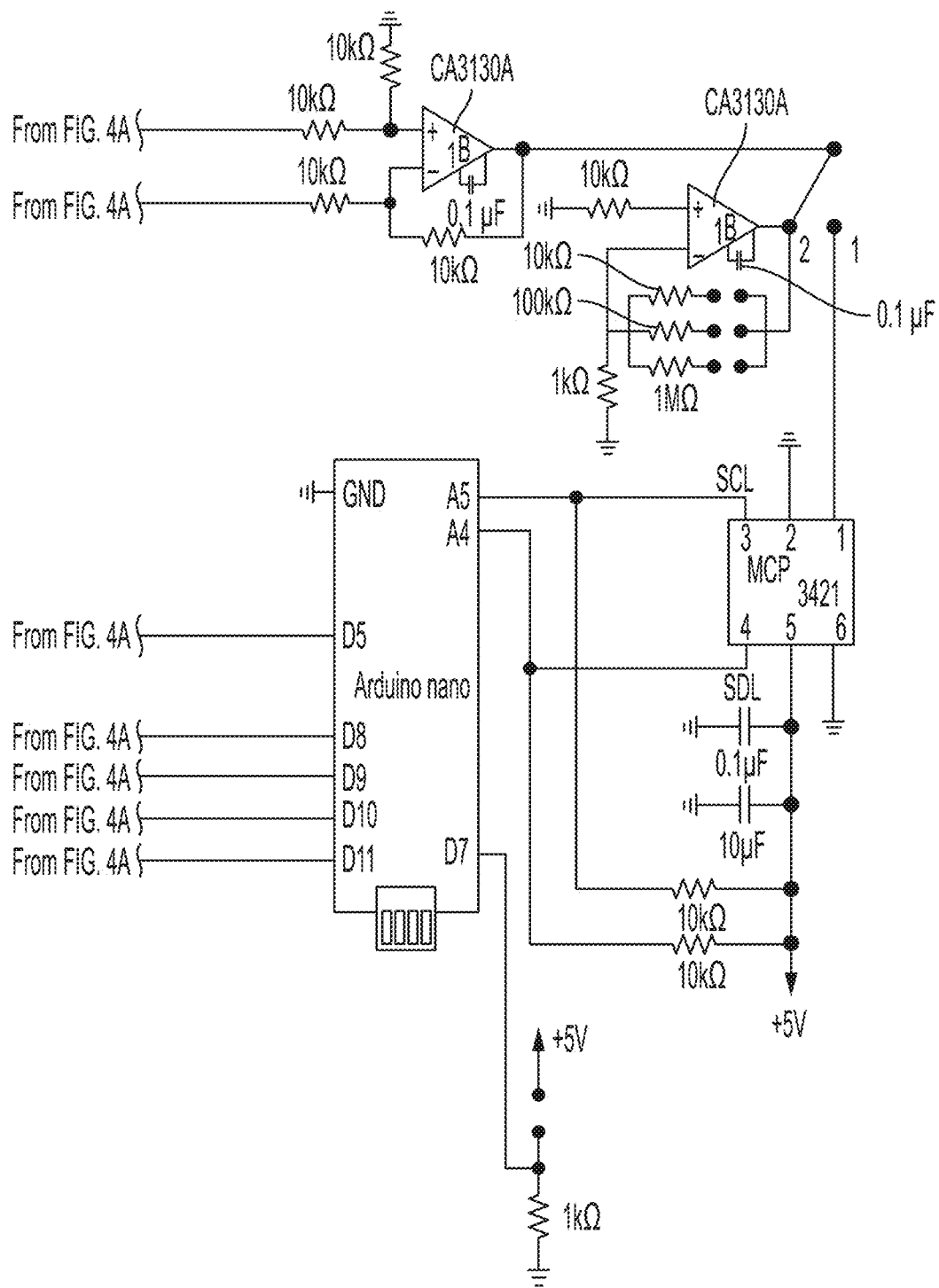
Figure 4C:
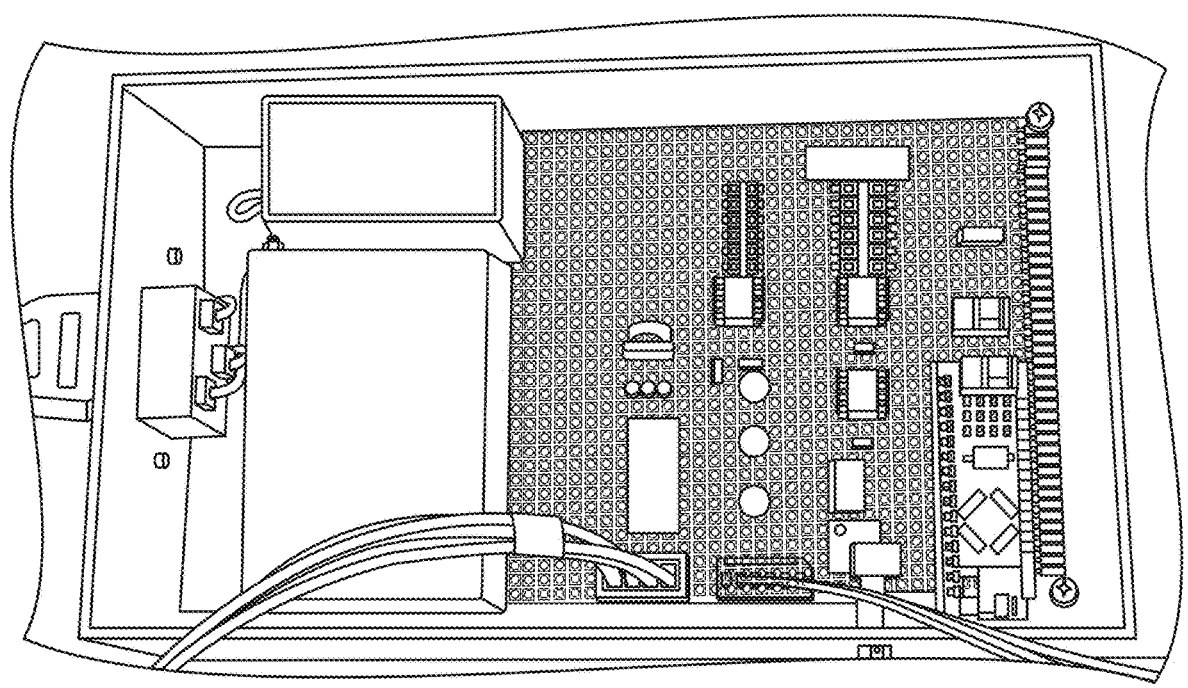

To read the MPPC analog output, the inventors developed an inexpensive and high resolution analog-to-digital converter (ADC). The ADC is a digitizer to convert analog signals to digitized values. A typical read range of ADC is 0-5 V and 4-20 mA for DC volt and current, respectively. The bit resolution of ADC varies depending on commercial products, generally in the range of 8-18 bit. The inventors also obtained an ADC (Microchip, MCP3421) which supports 12-18 bit resolution and inter-integrated circuit (I$^2$C) interface. To send the digitized values from ADC to computers or smart phones, a master device is required as a mediator. The inventors used Arduino microcontroller (Arduino, Nano Atmega328) as the master device for I$^2$C communication with ADC. The circuit diagram for the designed ADC is shown in FIG. 4. To program and implement I$^2$C protocol, the inventors used <Wire.h> in Arduino libraries.

Sample Loading and Measurement System

Figure 5:
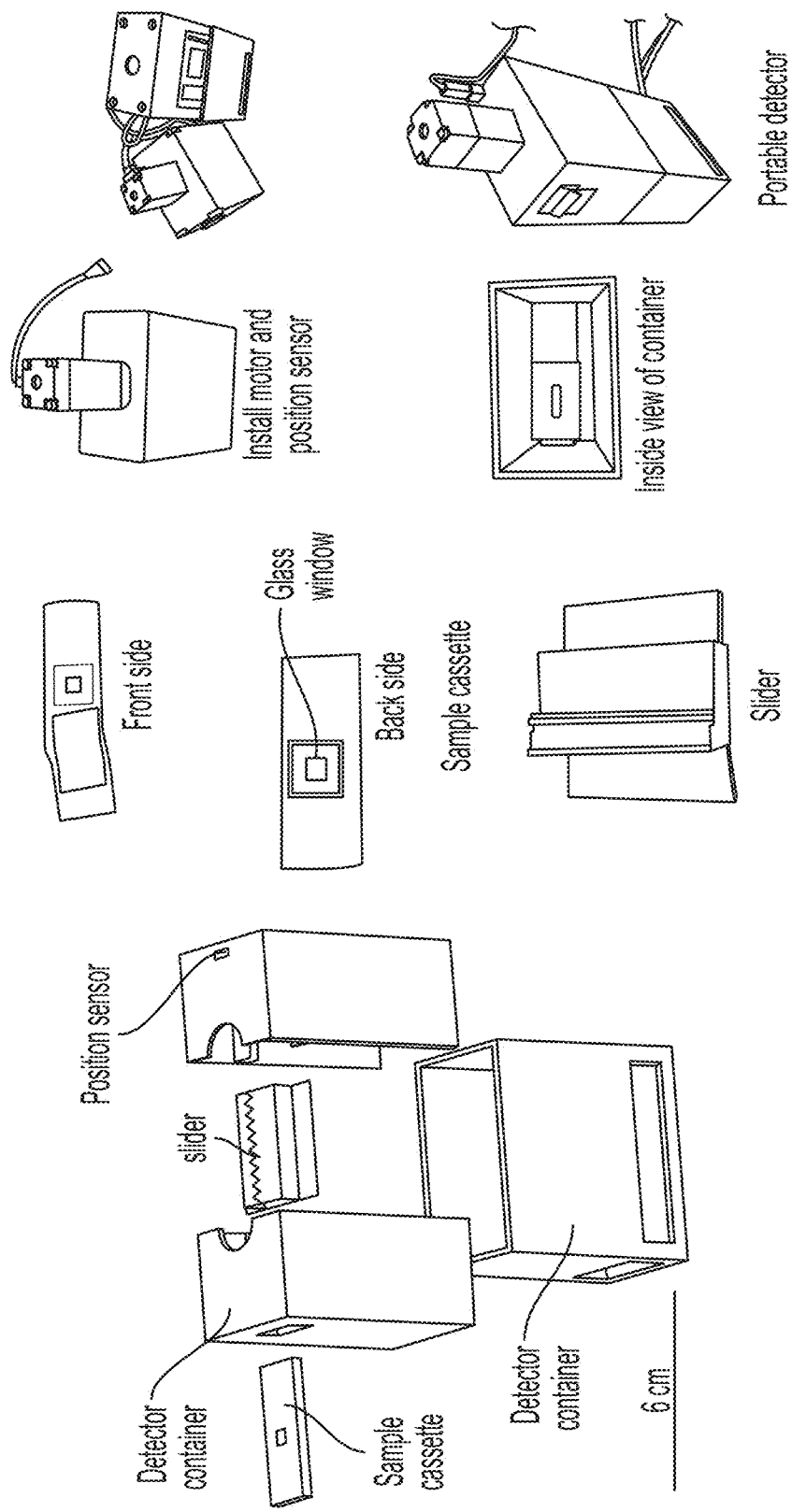
FIG. 5 illustrates a schematic of a sample loading and measurement system.

To develop a sample loading and measurement system, plastic prototype parts were created using a 3D modeling software (Autodesk, Inventor Professional 2015, student edition) and 3D printer (Flashforge, Creator Pro) as shown in FIG. 5. The inventors designed a disposable cassette in which a liquid sample is added. To mount the cassette on MPPC module, the stepper motor (Nema 8, 8HS11-0204S) brings the slider to the cassette door, and then users can insert the cassette into the slider. The slider carrying the cassette moves back and stops on the place where detector array is located. The light generated by the chemiluminescence reaction goes through the glass window of the cassette bottom and reaches to the detector arrays. The motor position is calibrated using the on-off sensor which is located in the opposite side of the cassette door. When the slider hits the position sensor, the sensor switches on to set the motor position as zero. The stepper motor is controlled using a quadruple half-H driver (Texas instrument, SN754410N). The circuit diagram for the motor driver is shown in FIG. 4. To program and implement the motor driver, the inventors used <AccelStepper.h> in Arduino libraries.

LabView Graphic User Interface (GUI)

Figure 6:
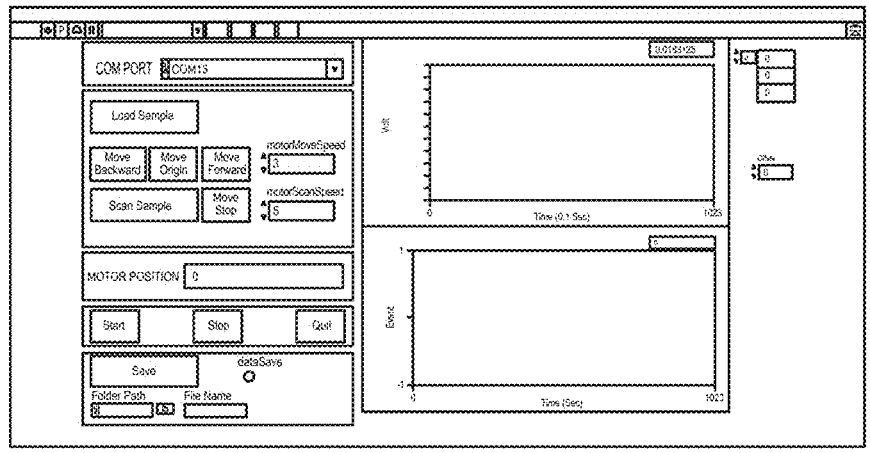
FIG. 6 illustrates a schematic of a graphic user interface (GUI) for data acquisition and MPPC operation.
Figure 6:
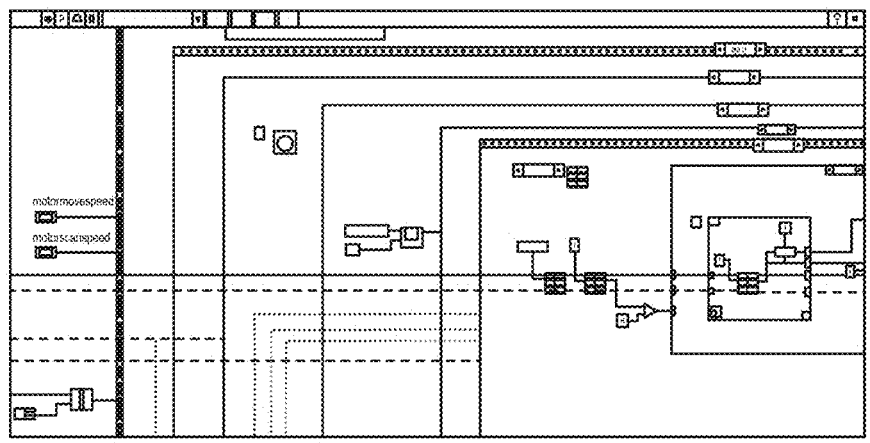

To operate the MPPC measurement system and to visualize acquired signals, a graphic user interface (GUI) was developed using LabView 8.6 (National Instrument) as shown in FIG. 6. The functions of the GUI are to send requests to and receive responses from the Arduino microcontroller to operate the ADC and stepper motor. The inventors adopted the serial interface for communication between the computer and the Arduino microcontroller, because both LabView and Arduino support serial interface and library. The commands for the serial communication are listed in Table 1 reproduced below.

TABLE 1

Protocols for serial communication

| Command | Request code | Response code | Error code |
|---|---|---|---|
| ADC Request Data | HASOT | HXXXT | • |
| Motor Stop | HMSOT | HXT | • |
| Motor Load Sample | HMLOT | HXT | • |
| Motor Move Origin | HMOOT | HXT | • |
| Motor Move Forward | HMFOT | HXT | • |
| Motor Move Backward | HMBOT | HXT | • |
| Motor Move Scan | HMMXT | HXT | • |
| Motor Get Position | HMPOT | HXT | • |

Detection of Horse Radish Peroxidase Conjugated Streptavidin (HRP-Streptavidin) Using MPPC To validate that the MPPC system can detect low level light, the inventors first determined concentrations of HRP-Streptavidin (Thermo Fisher Scientific, #21130) using the chemiluminescence assay. The inventors mixed 30 µL luminol solution (Michigan Diagnostics, FEMTOGLOW) with 10 µL HRP-Streptavidin at various concentrations, from 10 ng/mL to 100 pg/mL. The intensities for each sample were immediately measured using the MPPC. In the MPPC measurement, the sampling rate was 10 samples/sec and ADC resolution was set as 14 bit. To compare sensitivity of the MPPC with a commercial available instrument, the inventors performed HRP-Streptavidin measurement with Tecan microplate reader (Tecan, Infinite 200 PRO) as well.

Figure 7:
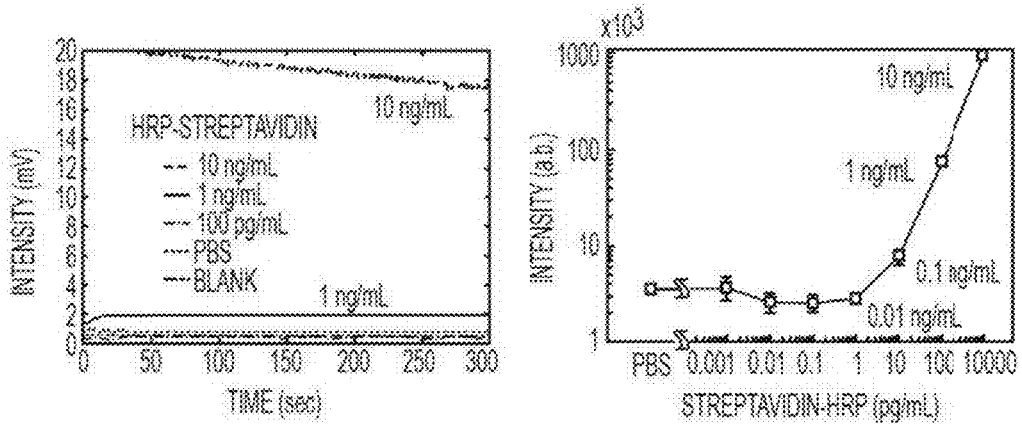
FIG. 7 illustrates a graph of detection of HRP-Streptavidin using MPPC and Tecan microplate reader.

The intensities read from the MPPC and Tecan reader were proportional to the concentration of HRP-Streptavidin as shown in FIG. 7. For the MPPC, the inventors detected 2 mV intensity for 1 ng/mL HRP-Streptavidin. Even though the 14-bit ADC has a resolution of 6.25 µV per bit, the inventors could not detect 0.1 ng/mL HRP-Streptavidin, whose signal is expected to be at 200 µV. This is because the background signal is as high as 600 µV. However, 0.1 ng/mL HRP-Streptavidin was detected using Tecan reader equipped with a photomultiplier tube (PMT). Therefore, the MPPC is about 10-times lower sensitivity than Tecan reader for the detection of the HRP-Streptavidin.

Detection of Hydrogen Peroxide ($H_2O_2$) Using MPPC

To determine that the MPPC can detect low level $H_2O_2$, the inventors measured $H_2O_2$ at various concentrations (1.7 mM-1.7 µM) using chemiluminescent assay. 30 µL of luminol solution (Michigan Diagnostics, customized FEMTOGLOW) was mixed with 10 µL of $H_2O_2$ and 10 µL HRP-Streptavidin, followed by measuring intensities using the MPPC and Tecan microplate reader. Note that the customized luminol solution does not contain $H_2O_2$.

The inventors also detected $H_2O_2$ using two different amount of HRP-Streptavidin, such as 10 and 1 µg/mL. If the concentration of HRP-Streptavidin is too high, the signal is decayed fast in a few seconds. In this case, one can miss signal generated at the beginning of the reaction during loading the sample in the cassette or plate. On the other hand, if the concentration of HRP-Streptavidin is too low, the reaction could not generate strong enough light to be measured. The inventors determined 17 µM and 1.7 µM as a limit of detection (LoD) of $H_2O_2$ for the MPPC and Tecan plate reader, respectively.

Detection of 1,5-AHG Using MPPC

Figure 9:
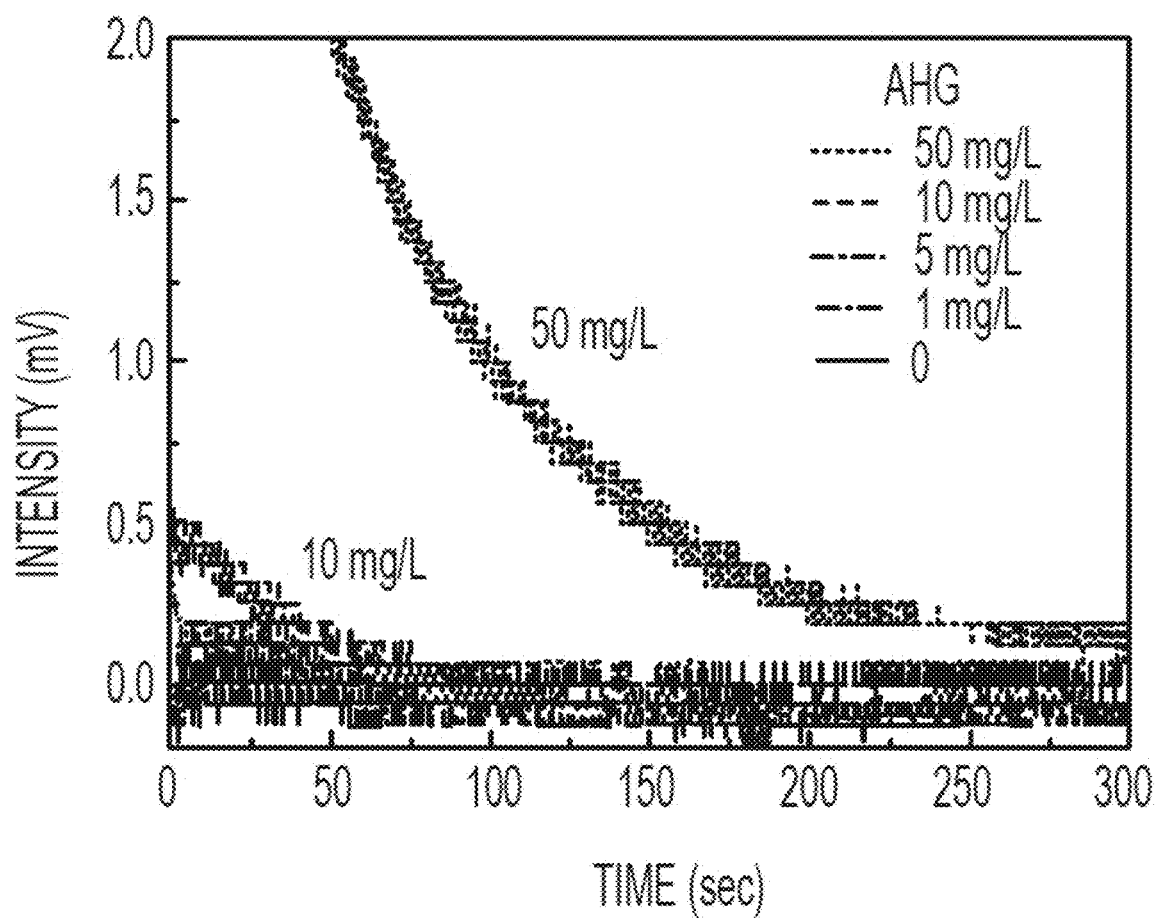
FIG. 9 illustrates a graph of detection of low level 1,5-AHG using MPPC.

To evaluate sensitivity of the MPPC for detecting low level 1,5-AHG, the inventors measured 1,5-AHG at various concentrations (50-1 mg/L) using chemiluminescent assay. Results are shown in FIG. 9. 10 µL of 1,5-AHG was mixed with 10 µL of 1 mg/mL PROD for 5 mins at room temperature. After the reaction of PROD and 1,5-AHG, 30 µL luminol solution (Michigan Diagnostics, customized FEMTOGLOW) and 10 µL of 1 µg/mL HRP-Streptavidin were added to the 1,5-AHG sample solution, followed by measuring intensities using the MPPC. The inventors evaluated 5 mg/L LoD of 1,5-AHG for the MPPC system.

Photomultiplier (PMT)

Figure 10:
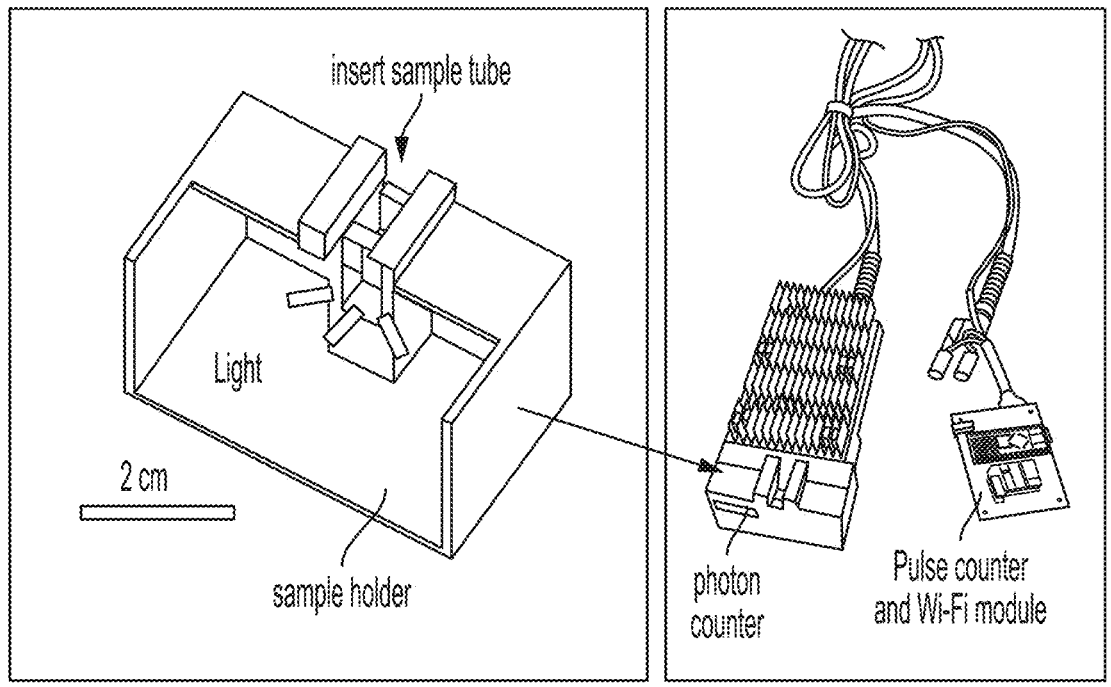
FIG. 10 illustrates a schematic of a sample holder and overall PMT system.

A photomultiplier (PMT) is a vacuum (~$10P^{-4}$) tube comprising an input window, a photocathode, focusing electrodes, an electron multiplier (dynodes) and an anode (last dynode). In principle, light first passes through the input window of PMT and excites the electrons in the photocathode. The excited electrons are accelerated and focused by the focusing electrodes, efficiently arriving at the first dynode. When hitting the dynode, the electrons are multiplied by emitting secondary electrons. This secondary emission is repeated at each of the successive dynodes. The multiplied secondary electrons are finally collected at the anode, generating the readable signal. The inventors obtained the photon counting head (Hamamatsu. H7421-50), detecting light in a dynamic range of 80 to $10^8$ photons. For the sample measurement, the inventors designed a sample holder as shown in FIG. 10.

Pulse Counter

The PMT generate a pulse signal whose width is 30 ns and height is 3.6 V. To count the number of output pulse, 14 MHz pulse counter is required due to 70 ns pulse-pair resolution. However, a 8 MHz pulse counter is good enough indeed for low level light, in fact that low level light generates less than ~1000 pulses per second. The inventors used the Arduino as the pulse counter which has an 8 MHz sampling speed. To program and implement the pulse counter, the inventors used <FreqCount.h> in Arduino libraries.

Wireless Data Acquisition System

Figure 11:
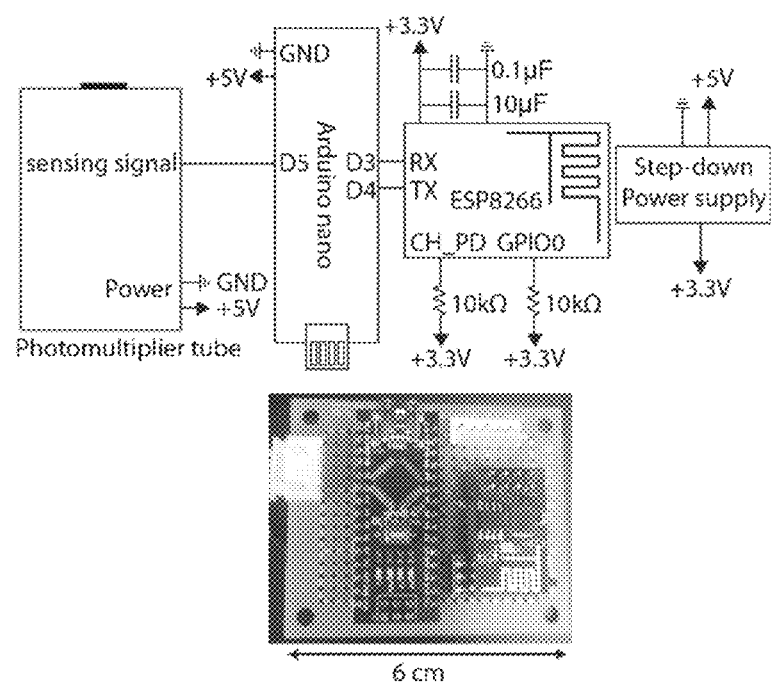
FIG. 11 illustrates a schematic of a circuit diagram for a wireless data acquisition system.

The inventors developed a wireless data acquisition system based on the smart phone and Wi-Fi networking. After Arduino counts the PMT pulse output, the counted number is sent to the smart phone through Wi-Fi. To do this, Wi-Fi interface is needed to mediate between the Arduino and smart phone. The ESP8266 (Espressif) is a programmable WiFi module equipped with serial port and digital input/output pins. ESP8266 provides access point (AP) mode and webserver service for clients. Unlike Wi-Fi direct and Bluetooth, multiple clients can access the ESP8266 webserver at distance up to 1 km. In principle of our wireless data acquisition system, the ESP8266 receives data from the Arduino through the serial port and saves it in the memory. Clients who connect to the AP of ESP8266 can requests the web service provided by ESP8266. Then, the web server responds hypertext transfer protocol (HTTP) containing a document written by hypertext markup language (html) through which data is transferred. To program the web server of the ESP8266, the inventors used the Arduino integrated development environment (IDE). The circuit diagram for the wireless data acquisition is shown in FIG. 11.

Android GUI

Figure 12:
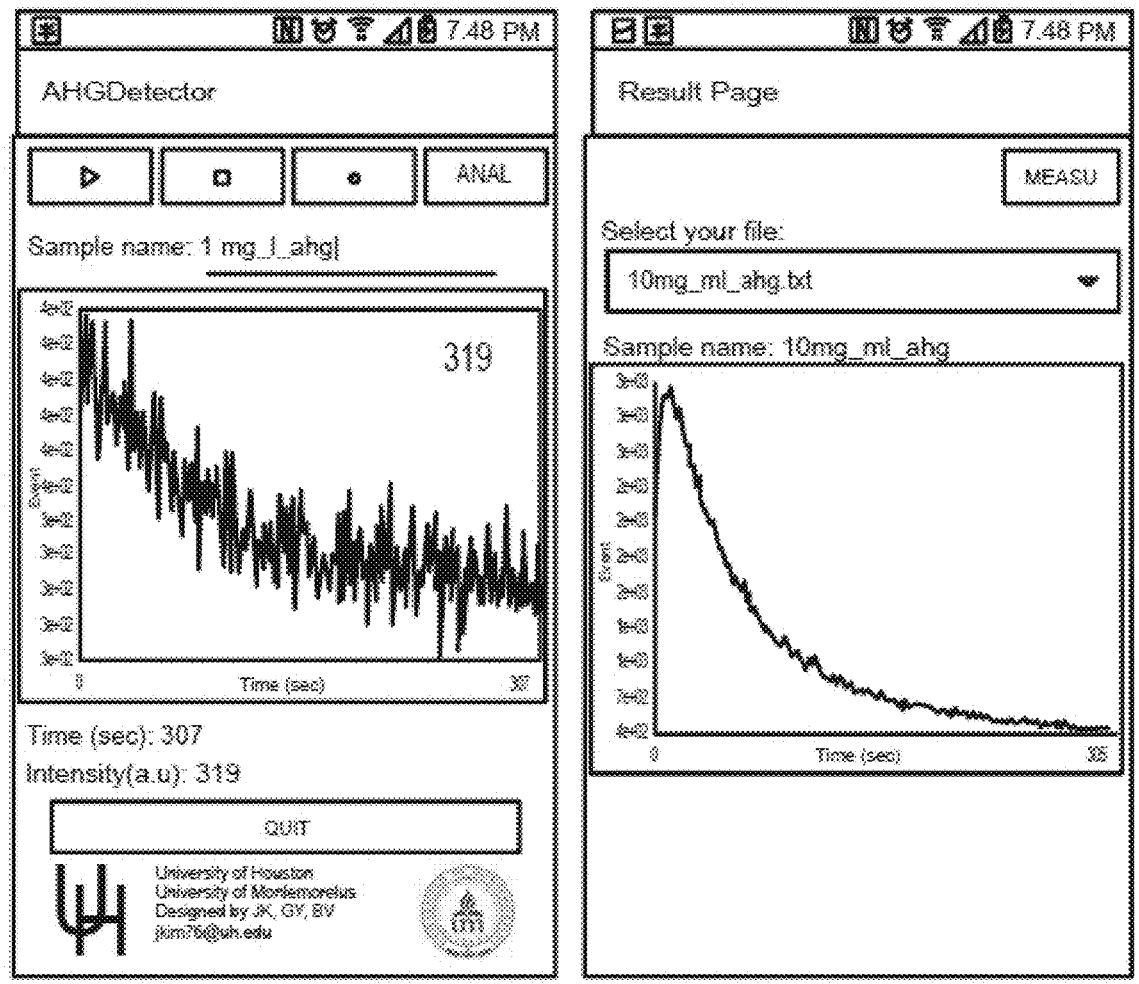
FIG. 12 illustrates a display of software application for 1,5-AHG measurement GUI.

To visualize acquired signals and assay results, graphic user interface (GUI) was required and developed using android studio which is one of the android application IDEs as an open source software. In one embodiment, an Android application comprises two activities, including measurement activity and result activity as shown in FIG. 12. The measurement activity performs data acquisition, data visualization and data save. After the measurement, the data is saved as a txt file in AHG_Data folder in the external device storage of the smart phone. Users can transfer and save the data file to computers through USB ports. The result activity shows the final measurement results and history data saved in the AHG_Data folder. The inventors will further modify the result activity to show data analysis. Unknown sample concentration will be determined and calculated based on a standardized curve. Experiments to obtain the standardized curve will be performed with known samples, after the PMT system is optimized.

Detection of Hydrogen Peroxide ($H_2O_2$) Using PMT

To determine that the PMT system can measure low level $H_2O_2$, the inventors measured $H_2O_2$ at various concentrations (1.7 mM-170 nM) using chemiluminescent assay. 30 µL of luminol solution (Michigan Diagnostics, customized FEMTOGLOW) is mixed with 10 µL of $H_2O_2$ and 10 µL of HRP-Streptavidin, followed by measuring intensities using the PMT.

Figure 13:
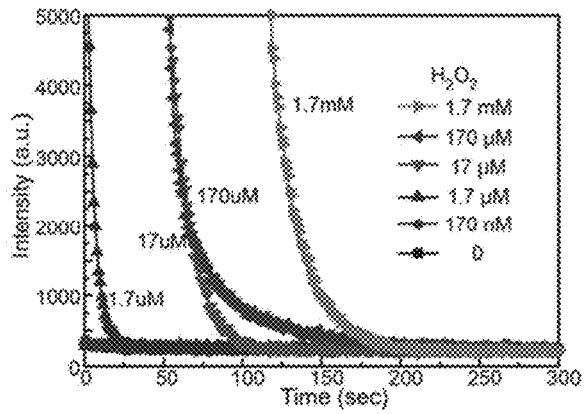
FIG. 13 illustrates graphs of detection of low level H2O2 using PMT.
Figure 13:
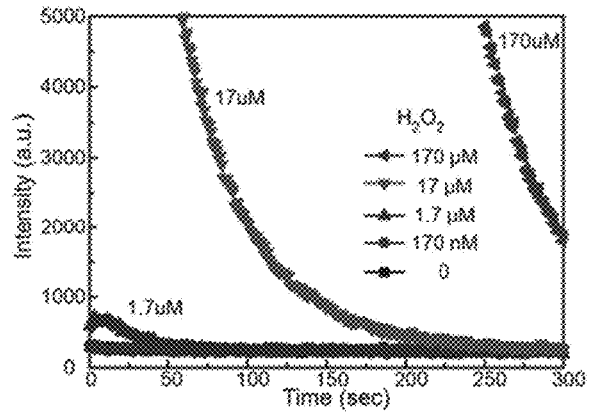

The intensities read from the PMT were proportional to the concentration of HRP-Streptavidin as shown in FIG. 13. The inventors determined 1.7 µM LoD of $H_2O_2$ which is three times higher than the dark count signal. The MPPC has similar sensitivity with Tecan microplate reader for LoD of $H_2O_2$.

Detection of 1,5-AHG Using PMT

To evaluate sensitivity of the PMT for detecting low level 1,5-AHG, the inventors measured 1,5-AHG at various concentrations (50-2 mg/L) using chemiluminescent assay. 10 µL of 1,5-AHG was mixed with 10 µL of 1 mg/mL PROD for 5 mins at room temperature. After the reaction of PROD and 1,5-AHG, 30 µL of luminol solution (Michigan Diagnostics, customized FEMTOGLOW) and 1 µg/mL HRP-Streptavidin were added to the 1,5-AHG solution, followed by measuring intensities using the PMT. The inventors determined 2 mg/L LoD of 1,5-AHG which is two times higher than the dark count signal at the beginning of the reaction as shown in FIG. 12.

Improved PMT System by Modifying Optical Path

Figure 14:
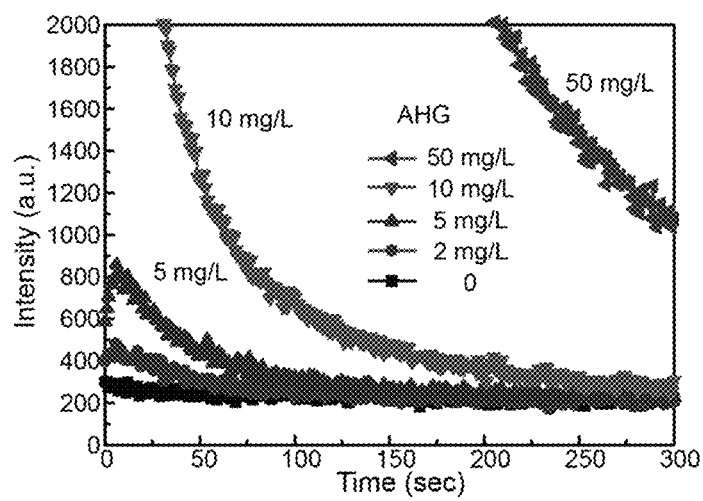
FIG. 14 illustrates a graph of detection of low level 1,5-AHG using PMT.
Figure 15:
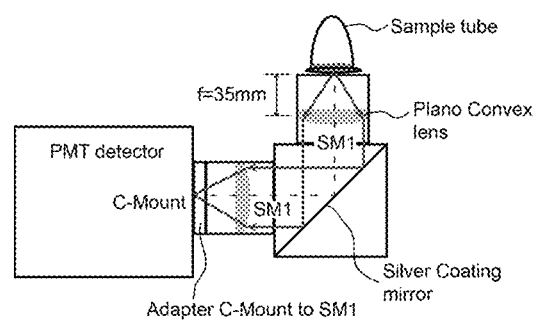
FIG. 15 illustrates a schematic drawing of an optical set-up for improving a PMT system.
Figure 16:
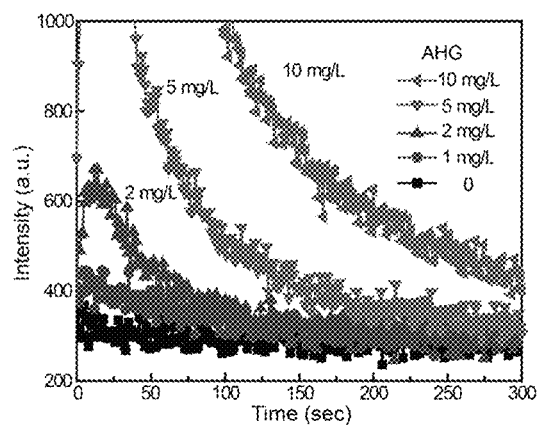
FIG. 16 illustrates a graph of improved detection of low level 1,5-AHG using PMT before optic alignment.

Only a tiny percentage of the light generated in the chemiluminescent reaction arrives at the photon sensor. Initial results of detection of low level 1,5-AHG using a PMT are shown in FIG. 14. To increase the intensity of the captured light, the inventors developed an optical set-up as shown in FIG. 15 to collimate and focus the chemiluminescent emission onto the photon sensor using plano-convex lenses. The inventors expected this optimization of the light path will increase the sensitivity by about twenty-fold. However, the inventors observed only two-fold improvement of the sensitivity (1 mg/L LoD) as shown in FIG. 16, compared to before optical set-up (2 mg/L LoD). The inventors assumed that the reduced improvement was based on a failure of optical alignment. After optical alignment was performed experimentally, the inventors had four-fold improvement of the sensitivity (0.5 mg/L LoD) as shown in FIG. 15, compared to before optical set-up (2 mg/L LoD).

Improved Signal-to-Noise Ratio—Cooling and Integration Time

Figure 17:
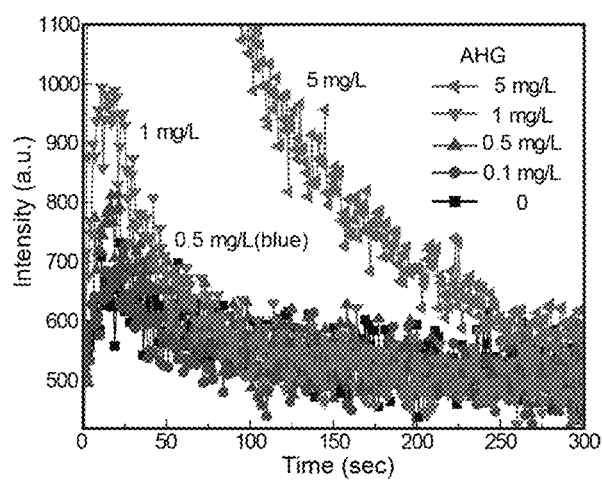
FIG. 17 illustrates a graph of improved detection of low level 1,5-AHG using PMT after optic alignment.
Figure 18:
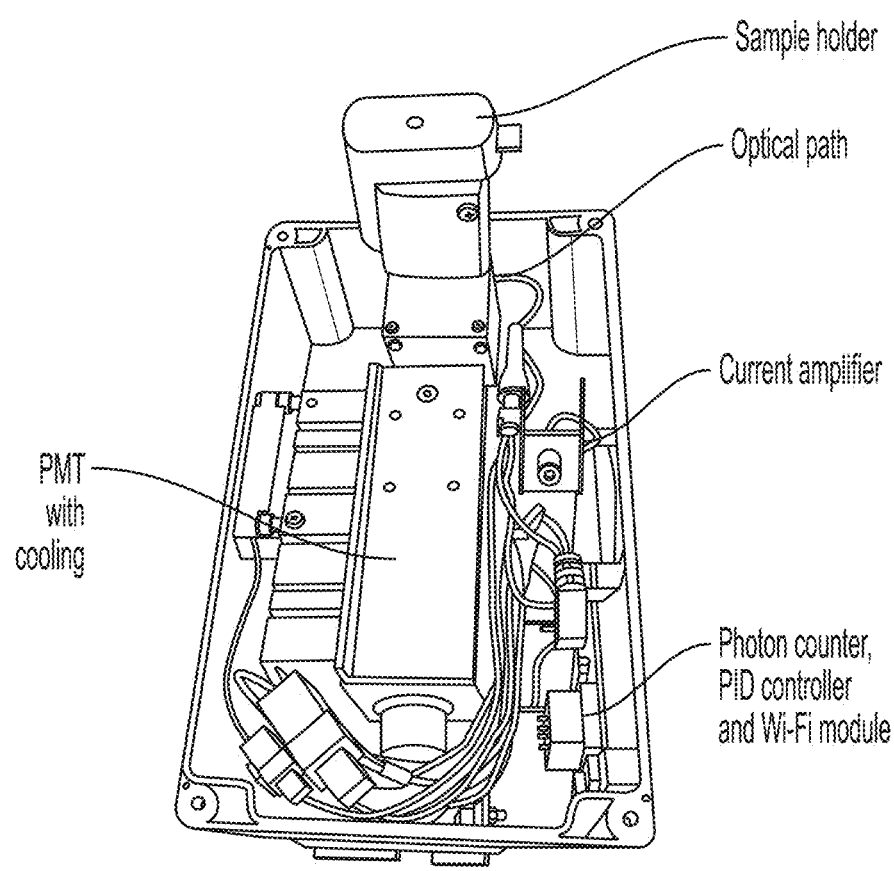
FIG. 18 illustrates a photograph of a complete PMT system with sensor cooling and optical path adjustment.
Figure 19:
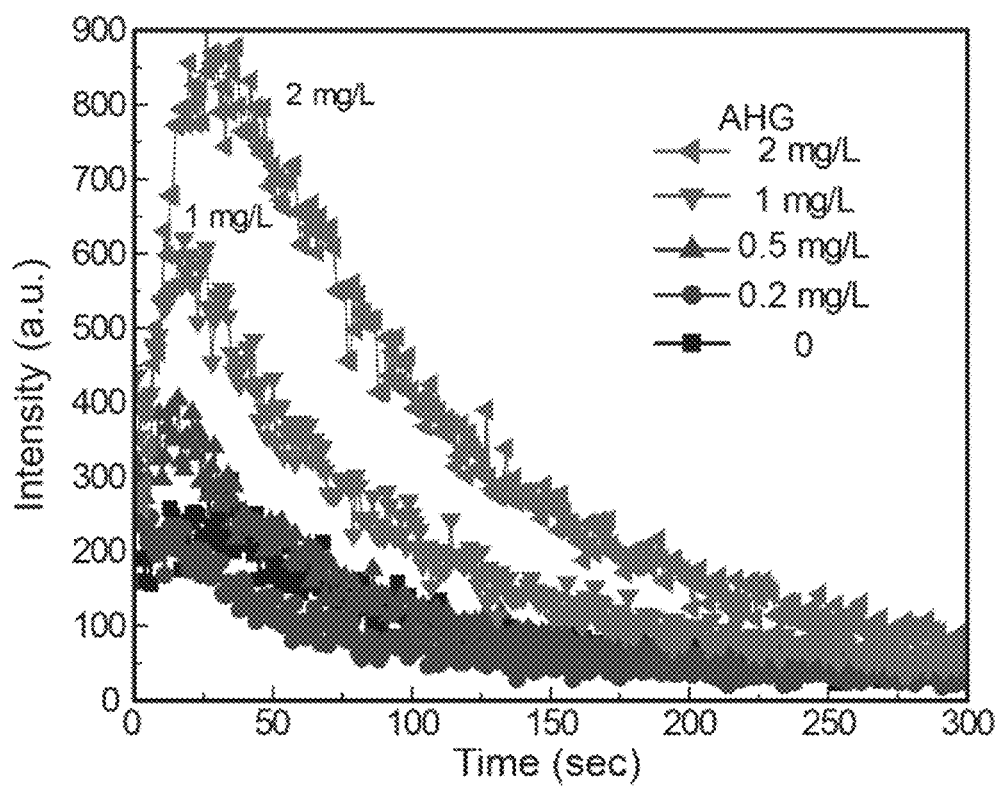
FIG. 19 illustrates a graph of improved SNR by removing dark counts.

Improving the signal-to-noise ratio (SNR) increases the sensitivity of the detector and hence lower the LoD of 1,5-AHG. FIG. 17 shows the signals with large fluctuation, leading to ambiguous decision between negative and positive control samples near LoD. With very low level of 1,5-AHG to generate more distinguishable signal than that of negative control sample, the improvement of SNR is desired. The SNR can be determined by equation:

$$SNR=(N\_S\sqrt{t})/\sqrt{(N\_S+2(N\_b+N\_d))}$$

where $N_s$ is the number of photons from chemiluminescent reaction, $N_b$ and $N_d$ are caused by background (or ambient) light and dark count, respectively, and t is integration time. From Equation (1), there are two ways to increase SNR. First, the inventors removed dark counts by cooling the sensor using a Peltier chip, whose temperature will be controlled at 0° C. using PID controller. The PID controller will be programmed using <PID_v1.h> in Arduino library. FIG. 18 shows the complete PMT system with sensor cooling and optical path adjustment. Before cooling, the sensor temperature was 24° C. at which the dark count was around 510. After cooling, the dark count decreased by 40 which provides two-fold improvement of SNR. FIG. 19 shows the reduced noisy signal with better SNR. However, 1,5-AHG LoD was still 0.5 mg/L which is same result before cooling detector.

Figure 20:
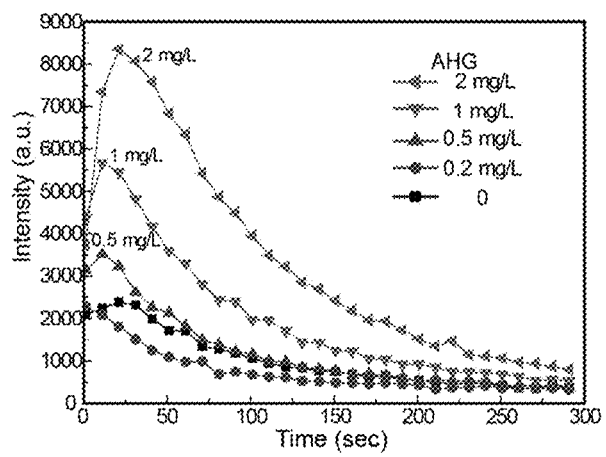
FIG. 20 illustrates a graph of improved SNR by removing dark counts and increasing integration time.

Secondly, the SNR can be improved by increasing the integration time. The number of photons is counted and accumulated during integration time. The inventors integrate the signals in FIG. 19 with 10 sec integration time, instead of 1 sec. FIG. 20 shows that a 10 second integration time gives much cleaner signals than that al second integration time.

Figure 8:
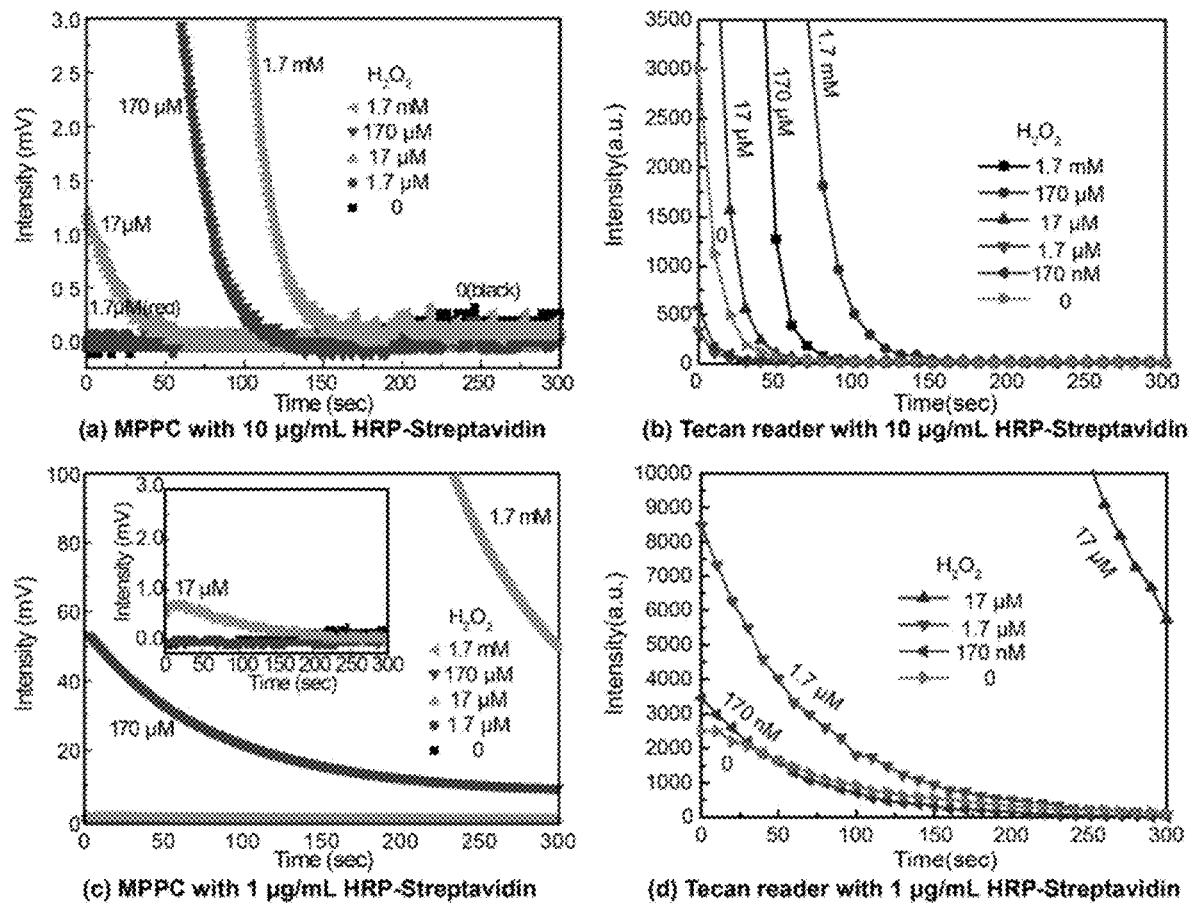
FIG. 8 illustrates a graph of detection of low level H2O2 using MPPC and Tecan reader.

The blank sample (water) showed unexpected signals. In the absence of $H_2O_2$, something precipitated the chemiluminescent reaction. The same result was also observed using Tecan plate reader in panel (b) of FIG. 8. The inventors did not yet identify the species which reacts with luminol and HRP and creates light emission, but the inventors suspect it may be oxygen dissolved in the water.

The specimen to be used in the present invention is body fluid to assay 1,5-AHG contained therein. An enzymatic chemiluminescent reaction will be carried out in order to emit light for detection with the apparatus disclosed in the present invention. One aspect of the present invention comprises removing all sugars such as glucose from such specimen that can react with the aforementioned chemiluminescent reaction, to give appropriate samples.

This can be carried out, for example, by using glucose phosphorylation or column depletion, according to the methods disclosed in Nowatzke W, et al. 2004. Clinica Chimica Acta. 350: 201-209 and Yabuuchi M, et al., 1989. Clin. Chem. 35/10, 2039-2043, respectively. Namely, Glucokinase or any other glucose phosphorylation enzyme is added to the saliva sample and the obtained mixture is incubated at the appropriate temperature and time, preferably at ambient temperature (20-40° C.), and from 5-10 minutes. This can be carried out alone or coupled to a depletion column method where the treated or untreated sample is passed through a column packed with a strong anion exchange resin to remove glucose, from sample.

Afterwards, an electron acceptor, preferably pyranose oxidase is employed to generate hydrogen peroxide, which is employed as a substrate for any number of available method that gives a chemiluminescent response in presence of any other substrates. The most commonly employed method employs the catalytic enzyme horseradish peroxidase (HRP) and luminol to show chemiluminescence.

All these elements will be put together in a single reaction kit compatible with the apparatus reason of the present invention, as long as they would not affect each other, and can be presented in an easily to use manner, for example, in powder or films or carried in a dry excipient. Furthermore, the whole kit should provide a standard reference in order to calibrate the apparatus. For further illustrate the present invention, the following examples are given.

EXAMPLES

Example 1: Detection of 1,5-AHG with Enzymatic Reaction Pretreatment

Early diagnosis of type 2 diabetes (T2D) is paramount important to reduce the complications of diabetes. For the glycemic monitoring in T2D, one can measure metabolic analytes, such as 1,5-anhydroglucitol (1,5-AHG), HbA1c and glucose in blood samples. Recent report has revealed a strong association of T2D with 1,5-AHG in saliva as a noninvasive marker, resulting in benefit of patients who adverse to blood sampling. 1,5-AHG is unmetabolizable glucose analogue which is present in human blood due predominantly to dietary ingestion. In physiology, 1,5-AHG level is balanced by being reabsorbed and excreted through kidney and urine, respectively. Normal range of 1,5-AHG level in human body is around 6.8-32.3 µg/ml. 1,5-AHG concentration in blood decreases during times of hyperglycemia, since reabsorption is completely inhibited by glucose at fructose and mannose active transporter; Therefore, monitoring 1,5-AHG in saliva is useful in achieving glycemic control.

Figure 1:
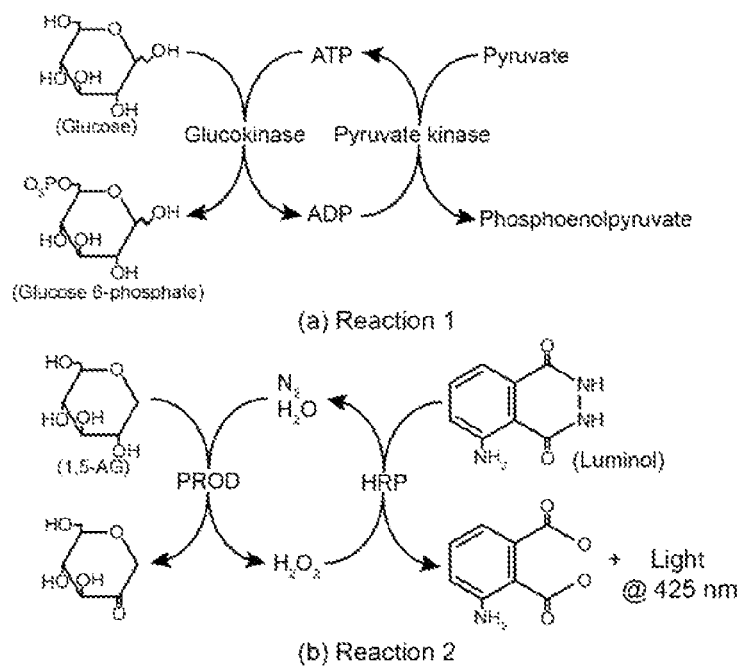
FIG. 1 illustrates a schematic of a reaction scheme for chemiluminescence-based detection of 1,5-AHG.

To determine the concentration of 1,5-AHG, conventional methods such as liquid chromatography, gas-liquid chromatography, HPLC, or mass spectrometry can be used. An alternative method is to use enzymatic reaction assay. Pyranose oxidase (PROD) has been used for determining D-glucose and 1,5-AHG in clinical analysis. PROD oxidizes the second position hydroxyl group of 1,5-AHG and generates hydrogen peroxide which can be detected using a variety of methods. Therefore, 1,5-AHG is indirectly determined by measuring the generated hydrogen peroxide as shown in reaction 2 of FIG. 1 section (b). However, saliva sample contains D-glucose, which is also oxidized by PROD and produces hydrogen peroxide, thus, interferes with 1,5-AHG measurement. In this case, pretreatment of the sample is required to keep D-glucose from reaction with PROD as shown reaction 1 of FIG. 1 section (a).

In this example, saliva sample containing 1,5-anhydroglucitol is pretreated with glucokinase to remove glucose. Glucose is converted into glucose-6-phosphate with the aid of an adenosine triphosphate (ATP)-regenerating system consisting of pyruvate kinase and phosphoenol pyruvate. After pretreatment, pyranose oxidase is mixed with the treated sample to catalyze the oxidation of 1,5-anhydroglucitol to hydrogen peroxide. After the reaction with pyranose oxidase, chemiluminescent substrate and horseradish peroxidase are added, then immediately followed light intensity measurement using high sensitivity light detector, such as CCD camera, PMT, avalanche diode, S-CMOS camera, CMOS camera, or high sensitivity smart phone camera, can be used to perform light intensity measurement of the lines. Intensity measurement is interpreted as 1,5-anhydroglucitol concentration.

In another modification, after the reaction of pyranose oxidase and 1,5-anhydroglucitol in sample, 30 µL of luminol solution and 1 µg/mL laccase are added to the 1,5-AHG solution, followed by measuring intensities using light detector.

In another modification of this example, after the reaction of pyranose oxidase and 1,5-anhydroglucitol in sample, aryl oxalate such as diphenyl oxalate and a fluorescent substance is added to the sample, hydrogen peroxide from the first reaction react with aryl oxalate in the presence of a fluorescent substance to thereby excite the fluorescent substance, thus emitting photons.

Example 2: Detection of 1,5-AHG with Chromatography Column

In an example, sample is run thru a chromatography column, such as ion exchange, HIC, metal chelate, boronate, or affinity, to remove glucose and other interferences. The eluent containing 1,5-anhydroglucitol is mixed with 10 µL of pyranose oxidase for 5 mins at room temperature. After the reaction of pyranose oxidase and 1,5-anhydroglucitol, 30 µL of luminol solution and 1 µg/mL peroxidase are added to the 1,5-AHG solution, followed by light intensity measurement using the point-of-care (POC) photon detector.

Example 3: Additional Sample Pretreatment to Remove Interferences

Depending on the sample sources, the presence of some monosaccharides can interfere with the 1,5-AHG detection assay. Some of the known interferences when using pyranose oxidase as 1,5-AHG detection enzyme include: D-glucose, L-sorbose, D-xylose, D-galactose, glucono-δ-lactone. The complexity of pretreatment varies with the type of body fluids. Normally, with blood sample, D-glucose is the major interference and the pretreatment methods were described in example 1 and 2. For samples from other body fluids, a mixture of enzymes is used instead of just glucose oxidase. Such enzyme mix contains enzymes that can convert or modify the interferences to non-interfering molecules. An example of composition of the enzyme mix includes glucose oxidase, L-sorbose oxidase, D-xylose oxidase, D-galactose oxidase, glucono-δ-lactone oxidase.

Example 4: Detection of 1,5-AHG with Dual Readout (Glucose and 1,5-AHG)

In an example, sample containing 1,5-anhydroglucitol is mixed with 10 µL of enzyme mix containing glucose oxidase, peroxidase and chemiluminescent substrate, then immediately followed by light intensity measurement using the point-of-care (POC) photon detector. The light signal is interpreted as glucose concentration. After the first reaction completed, pyranose oxidase is added then immediately followed by light intensity measurement using the high sensitivity light detector. The signal is interpreted as 1,5-anhydroglucitol concentration. The ratio of 1,5-anhydroglucitol to glucose can be used to correct for the variations in sample collection method.

Example 5: Detection of 1,5-AHG with Metal Nanoparticles as Chemiluminescent Catalyst In an example, sample containing 1,5-anhydroglucitol is mixed with 10 µL of enzyme mix containing glucose oxidase, nanoparticles such as silver nanoparticles, gold nanoparticles, platinum nanoparticles, iron oxide nanoparticles, nanoporous metal particles, or other metal catalysts, and chemiluminescent substrate, then immediately followed by light intensity measurement using the point-of-care (POC) photon detector. The light signal is interpreted as glucose concentration. After the first reaction completed, pyranose oxidase is added then immediately read light intensities using the point-of-care (POC) photon detector. The signal is interpreted as 1,5-anhydroglucitol concentration.

In another example, sample containing 1,5-anhydroglucitol is mixed with 10 µL of reaction mix containing glucose oxidase, and chemiluminescent substrate in a reaction chamber coated with catalyst that can catalyze hydrogen peroxide, then immediately followed by light intensity measurement using the point-of-care (POC) photon detector. The light signal is interpreted as glucose concentration. After the first reaction completed, pyranose oxidase is added then immediately read light intensities using the point-of-care (POC) photon detector. The signal is interpreted as 1,5-anhydroglucitol concentration.

In another example, sample containing 1,5-anhydroglucitol is split into two equal volume fractions. The first fraction is mixed with 10 µL of enzyme mix containing glucose oxidase, peroxidase and chemiluminescent substrate, then immediately followed by light intensity measurement using the point-of-care (POC) photon detector. The light signal is interpreted as glucose concentration. The second fraction is mixed with pyranose oxidase and chemiluminescent substrate then followed by light intensity measurement using the point-of-care (POC) photon detector. The signal is interpreted as the total concentration of glucose and 1,5-anhydroglucitol. 1,5-anhydroglucitol concentration is calculated from the two signals or by lookup table.

Example 6: Detection of 1,5-AHG in Microfluidic Device

In an example, the sample is applied to a microfluidic device in which the interferences such as glucose are removed as the sample passing thru the chromatographic column. The effluent is then mixed with pyranose oxidase. After the reaction of pyranose oxidase, sample is mixed with chemiluminescent reagent and horseradish peroxidase, followed by light intensity measurement thru the optical window with a high sensitivity light detector, such as CCD camera, PMT, avalanche diode, S-CMOS camera, CMOS camera, or high sensitivity smart phone camera In another example, the sample is applied to a microfluidic device then inserted into a reader, in which the sample is split into two fractions by the Y-junction in microfluidic channel. The fractions are pumped to two separated reaction chambers. In the first reaction chamber, a solution containing glucose oxidase is pumped in and mixed with the sample to produce hydrogen peroxide from oxidation of glucose. In the second chamber, reaction buffer containing pyranose oxidase is pumped and mixed in to produce hydrogen peroxide from oxidation of glucose and 1,5-anhydroglucitol. After a specific time which allows the reactions to complete, the content of the first reaction chamber is mixed with horseradish peroxidase and chemiluminescent substrate and followed by light intensity measurement thru the optical window with a (POC) photon detector. The signal from the first chamber is interpreted as glucose concentration. The content of the second reaction chamber is mixed with horseradish peroxidase and chemiluminescent substrate and followed by light intensity measurement thru the optical window with a (POC) photon detector. The signal is interpreted as the total concentration of glucose and 1,5-anhydroglucitol. 1,5-anhydroglucitol concentration is calculated from the two signals or by lookup table using the values of the signals.

In another example, the sample containing 1,5-anhydroglucitol is applied to a microfluidic device then inserted into a reader. The sample is pumped into reaction chamber and mixed with 10 µL of enzyme mix containing glucose oxidase, peroxidase and chemiluminescent substrate, then immediately followed by light intensity measurement thru an optical window. Glucose oxidase converts glucose to hydrogen peroxide which, in turn, reacts with chemiluminescent substrate catalyzed by horseradish peroxidase to generated light signal. The light signal is interpreted as glucose concentration. After the first reaction completed, when all glucose is used up, pyranose oxidase is mixed in then immediately followed by light intensity measurement thru an optical window. Pyranose oxidase converts 1,5-anhydroglucitol to hydrogen peroxide which, in turn, reacts with chemiluminescent substrate catalyzed by horseradish peroxidase to generated light signal. The signal is interpreted as 1,5-anhydroglucitol concentration.

Example 7: Detection of 1,5-AHG in Lateral Flow Assay (LFA) Format

In another example, sample containing 1,5-anhydroglucitol is mixed with horseradish peroxidase and chemiluminescent substrate. The sample and reagent mixture is then applied to a membrane strip using lateral flow assay (LFA) technology. The membrane strip is composed of nitrocellulose, glass fiber membrane such as Fusion 5, cellulose membrane, or any material that has wicking capability. The strip contains two enzyme lines, with glucose oxidase is the first line and pyranose oxidase as the second line that sample will encounter as it travels along the strip. As the sample moves over the glucose oxidase line (first line), glucose is oxidized by glucose oxidase to hydrogen peroxide. Hydrogen peroxide reacts with chemiluminescent substrate with horseradish peroxidase as the enzyme to produce light signal at the first line. The glucose depleted sample then travels to the second line where pyranose oxidase converts 1,5-anhydroglucitol to hydrogen peroxide. Hydrogen peroxide reacts with chemiluminescent substrate with horseradish peroxidase as the enzyme to produce light signal at the second line. High sensitivity light detector, such as CCD camera, PMT, avalanche diode, S-CMOS camera, CMOS camera, or high sensitivity smart phone camera, can be used to perform light intensity measurement of the lines. Intensity measurement from the first line is interpreted as glucose concentration, and the intensity measurement from the second line is interpreted as 1,5-anhydroglucitol concentration.

In another modification, sample containing 1,5-anhydroglucitol is mixed chemiluminescent substrate. The sample and substrate mixture is then applied to a membrane strip using lateral flow assay (LFA) technology. The membrane strip is composed of nitrocellulose, glass fiber membrane such as Fusion 5, cellulose membrane, or any material that has wicking capability. The strip contains four enzyme lines: the first line is glucose oxidase, second line is horseradish peroxidase, the third line is pyranose oxidase, and the fourth line as is horseradish peroxidase. The ordering is in the flow direction of sample that will encounter as it travels along the strip. The widths of the first and second lines are separately determined by the enzymatic reaction times of each enzymes. As the sample move over the glucose oxidase line (first line), glucose is oxidized by glucose oxidase to hydrogen peroxide. Hydrogen peroxide reacts with chemiluminescent substrate with horseradish peroxidase on the second line as the enzyme to produce light signal at the second line. The glucose depleted sample then travels to the third line where pyranose oxidase converts 1,5-anhydroglucitol to hydrogen peroxide. Hydrogen peroxide reacts with chemiluminescent substrate with horseradish peroxidase on the fourth line as the enzyme to produce light signal at the fourth line. High sensitivity light detector, such as CCD camera, PMT, avalanche diode, S-CMOS camera, CMOS camera, or high sensitivity smart phone camera, can be used to perform light intensity measurement of the lines. Intensity measurement from the second line is interpreted as glucose concentration, and the intensity measurement from the fourth line is interpreted as 1,5-anhydroglucitol concentration.

In another modification, sample containing 1,5-anhydroglucitol is mixed with chemiluminescent substrate. The sample and substrate mixture is then applied to a membrane strip using lateral flow assay (LFA) technology. The membrane strip is composed of nitrocellulose, glass fiber membrane such as Fusion 5, cellulose membrane, or any material that has wicking capability. The strip contains two enzyme lines, with mixture of glucose oxidase and horseradish peroxidase as the first line and mixture of pyranose oxidase and horseradish peroxidase as the second line, in which sample will encounter as it travels along the strip. As the sample move over the glucose oxidase line (first line), glucose is oxidized by glucose oxidase to hydrogen peroxide. Hydrogen peroxide reacts with chemiluminescent substrate with horseradish peroxidase as the enzyme to produce light signal at the first line. The glucose depleted sample then travels to the second line where pyranose oxidase converts 1,5-anhydroglucitol to hydrogen peroxide. Hydrogen peroxide reacts with chemiluminescent substrate with horseradish peroxidase as the enzyme to produce light signal at the second line. High sensitivity light detector, such as CCD camera, PMT, avalanche diode, S-CMOS camera, CMOS camera, or high sensitivity smart phone camera, can be used to perform light intensity measurement of the lines. Intensity measurement from the first line is interpreted as glucose concentration, and the intensity measurement from the second line is interpreted as 1,5-anhydroglucitol concentration.

In another example, 1,5-anhydroglucitol can be detected and measured in an indirect competitive chemiluminescent-lateral flow assay. The membrane strip is composed of nitrocellulose, glass fiber membrane such as Fusion 5, cellulose membrane, or any material that has wicking capability. The strip contains two lines: test line and control line. The test is an area where anti-1,5-anhydroglucitol antibody is immobilized. The control line is an area where anti-HRP antibody is immobilized. Sample containing 1,5-anhydroglucitol is mixed with known amount of HRP-1,5-anhydroglucitol conjugate. The mixture is applied to the membrane strip and migrates along the strip by capillary action. When reaching the area of the strip where the anti-1,5-anhydroglucitol antibody is immobilized, the 1,5-anhydroglucitol in the sample competed with HRP-1,5-anhydroglucitol for binding a fixed and limited amount of immobilized anti-1,5-anhydroglucitol antibody. Unbound reagents continued to migrate until they reached the area of the strip where excess HRP-1,5-anhydroglucitol conjugate was captured by immobilized anti-HRP antibody. In the detection step, a chemiluminescent substrate for HRP is added to the strip and the resulting chemiluminescent signal is imaged using the high sensitivity light detector, such as CCD camera, PMT, avalanche diode, S-CMOS camera, CMOS camera, or high sensitivity smart phone camera.

Example 8: Detection of 1,5-AHG in Competitive Chemiluminescent Enzyme-Linked Immunosorbent Assay (ELISA) Format In another example, 1,5-anhydroglucitol can be detected and measured in an indirect competitive chemiluminescent enzyme-linked immunosorbent assay (ELISA). The sample well is coated with anti-1,5-anhydroglucitol antibody. Sample containing 1,5-anhydroglucitol is mixed with known amount of HRP-1,5-anhydroglucitol conjugate. The mixture is added to the sample well and incubate for 30 minutes. The 1,5-anhydroglucitol in the sample competed with HRP-1,5-anhydroglucitol for binding a fixed and limited amount of immobilized anti-1,5-anhydroglucitol antibody. After incubation, unbound reagents are washed with a plate washer. In the detection step, a chemiluminescent substrate for HRP is added to the well and the resulting chemiluminescent signal is read using the plate reader.

Figure 21:
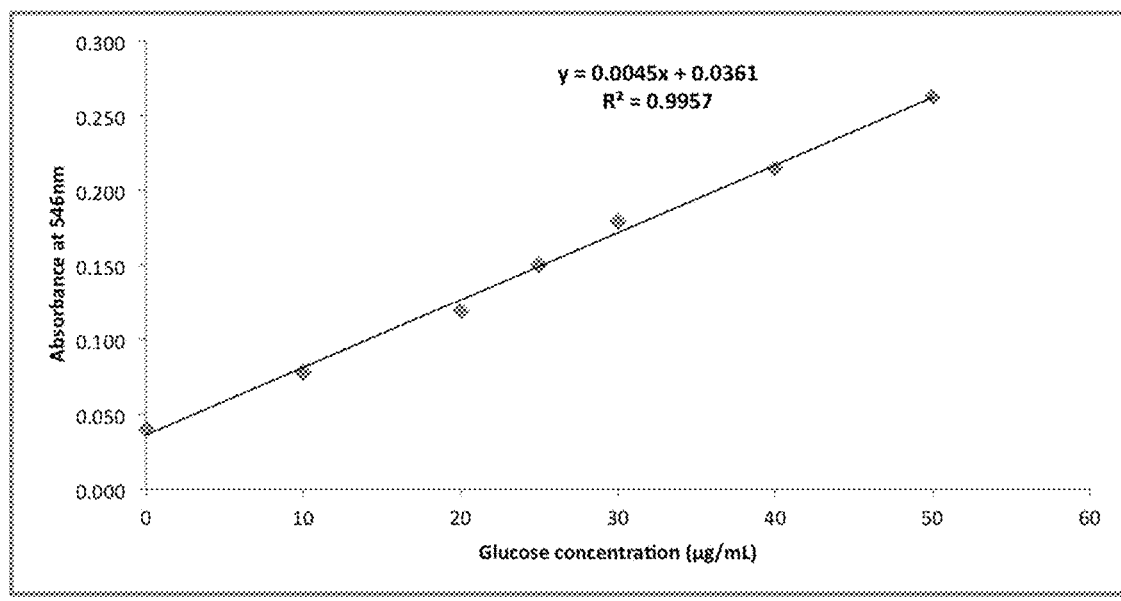
FIG. 21 illustrates a graph of a calibration curve for determining glucose with the use of glucose oxidase.

Example 9: Calibration Curve for Determining Glucose with the Use of Glucose Oxidase Phosphate buffer (monobasic and dibasic sodium phosphate) pH 6.5 at 0.2 M, TRIS-HCl Buffer, pH 8.5 at 50 mM, 3-(N-Ethyl-3-methylanilino)-2-hydroxy-propanesulfonic acid sodium salt (TOOS) at 10 mg/mL, 4-Aminoantipyrine (4-APP) 14 mg/mL, Glucose Oxidase at 18.3 U/mL, and HRP at 0.57 mg/mL (194 U/mg). 40 uL of a given dilution of glucose standard with 50 ug/mL concentration are mixed with 60 uL of a reagent containing 1 mL of TOOS, 1 mL of 4-APP, 1 mL of HRP and 7 mL of TRIS-HCl and 60 uL and 80 uL of a reagent containing 50 mL of phosphate buffer pH 6.5 and 5 mg of Glucose Oxidase. After 5 minutes, the absorbance of the reaction, carried out in transparent microplates of 96 wells is read at a wavelength of 546 nm in an Epoch reader (BioTek). The calibration curve can be created from the results (shown in FIG. 21).

Figure 22:
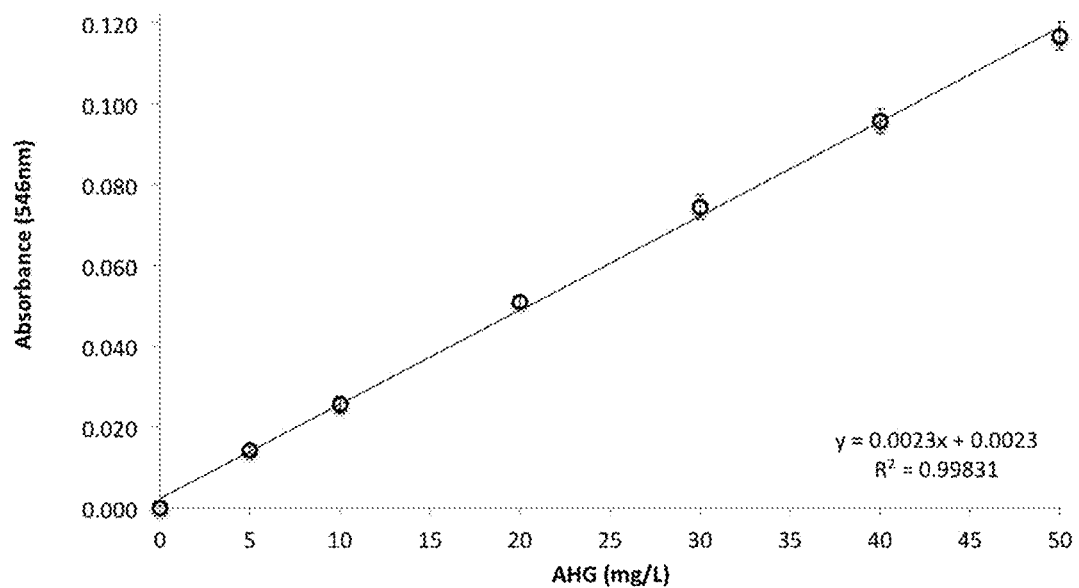
FIG. 22 illustrates a graph of a calibration curve for determining 1,5-AHG with the use of pyranose oxidase.

Example 10: Calibration Curve for Determining 1,5-AHG with the Use of Pyranose Oxidase 160 uL of a final reaction containing 32.14 mM of TRIS-HCl, pH 9, 10.71 mM of $MgCl_2$, 2.14 mM of ATP, 6.25 U/mL of Glucokinase, 6.56 mM of TRIS-HCl pH 8.5, 6.35 mM of TOOS, 129.16 mM of 4-APP, 1.07 U/mL of HRP and 2.18 U/mL of pyranose oxidase, with the correspondent dilutions of 1,5-AHG at 50 mg/mL are taken and absorbance read at 546 nm. The calibration curve can be created from the results (shown in FIG. 22).

Example 11: Assay of Glucose Depletion with Use of Pretreatment Column

Figure 23:
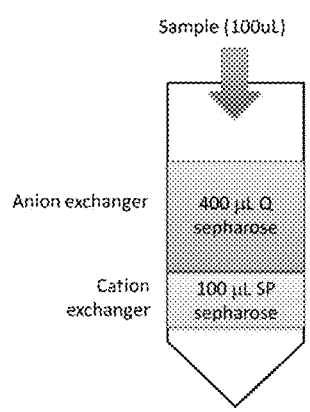
FIG. 23 illustrates a schematic of a glucose depletion using pretreatment column.
Figure 24:
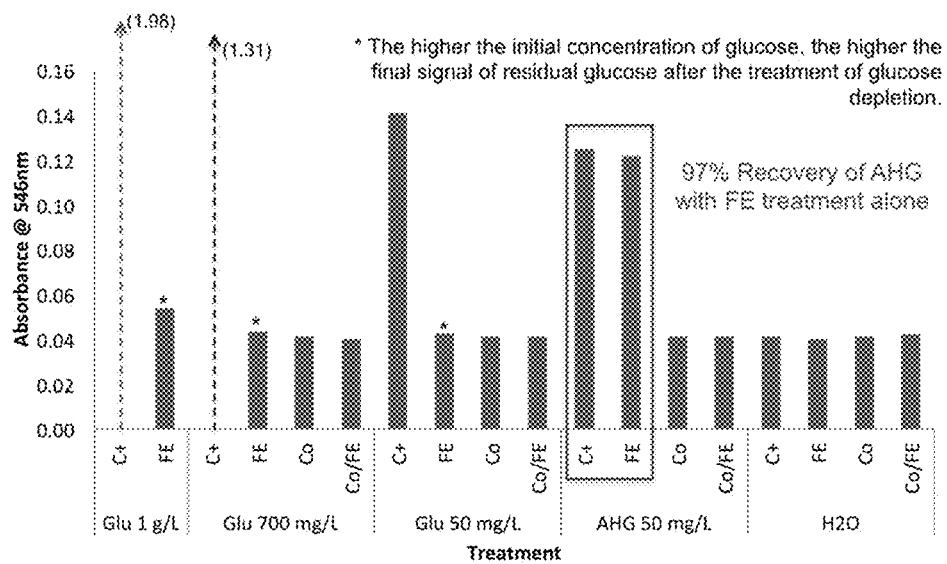
FIG. 24 illustrates a chart of separation efficiency using a minicolumn for glucose depletion in mixture with 1,5-AHG.

A column is filled with 100 uL of SP Sepharose (cation exchanger, user for the equilibration of the effluent), followed by 400 uL of Q Sepharose (anion exchanger) (shown in FIG. 23). The column is washed with 500 uL of water (3×). After this, 100 uL of a sample, namely glucose or 1,5-AHG, are passed through the column. 10 uL of the effluent are assayed. Results are shown in FIG. 24.

Example 12: Light Kinetics Obtained with the Use of HRP and Luminol

Figure 25:
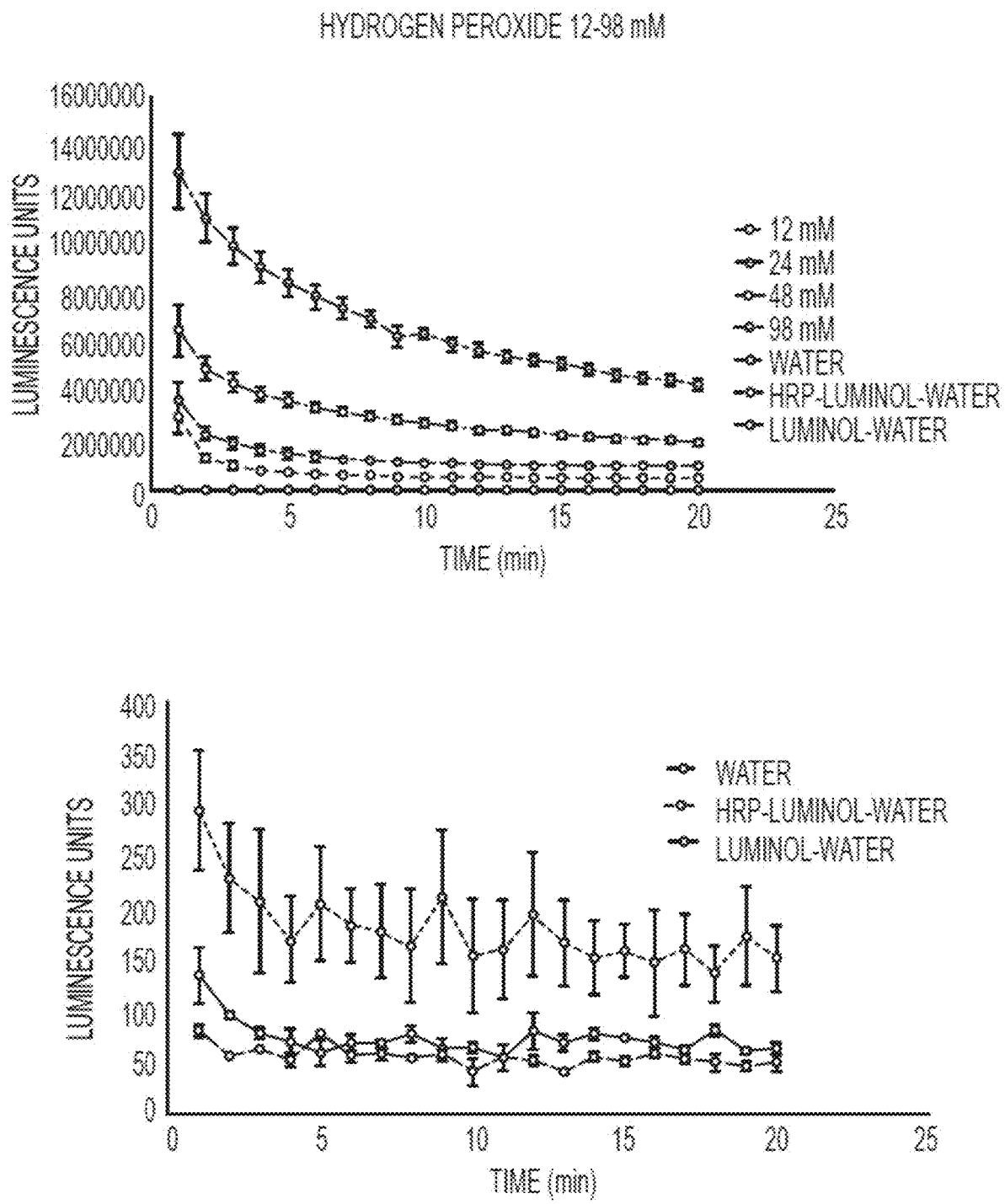
FIG. 25 illustrates a graph of chemiluminescent kinetics obtained with the use of HRP and luminol.

The reagents employed for this experiment are: HRP solution (270 ng/mL), $H_2O_2$ solutions (12.3-98 mM) and luminol (0.424 mg/L). These reagents are mixed in the next proportion in a black microplate: 35 uL of HRP, 75 uL of luminol and 50 uL of $H_2O_2$. Microtiter plate was placed in luminometer and measurements were taken every minute for 20 minutes. The correspondent results are shown in FIG. 25.

Figure 26:
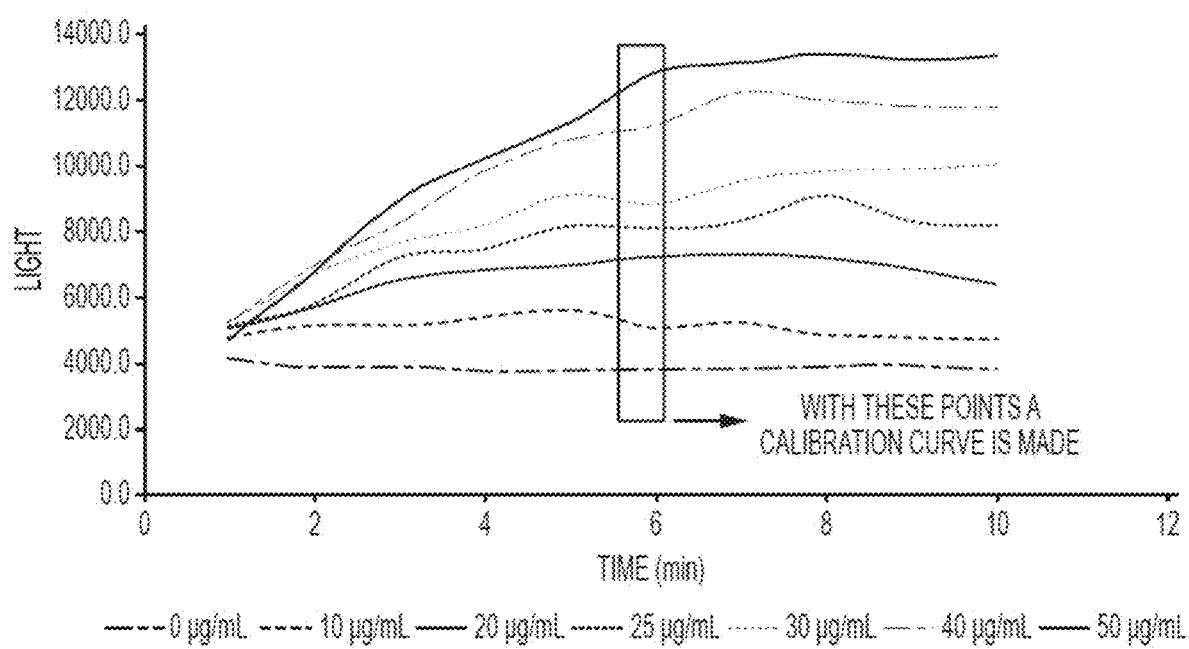
FIG. 26 illustrates a graph of reaction kinetic curve of 1,5 AHG assay.
Figure 27:
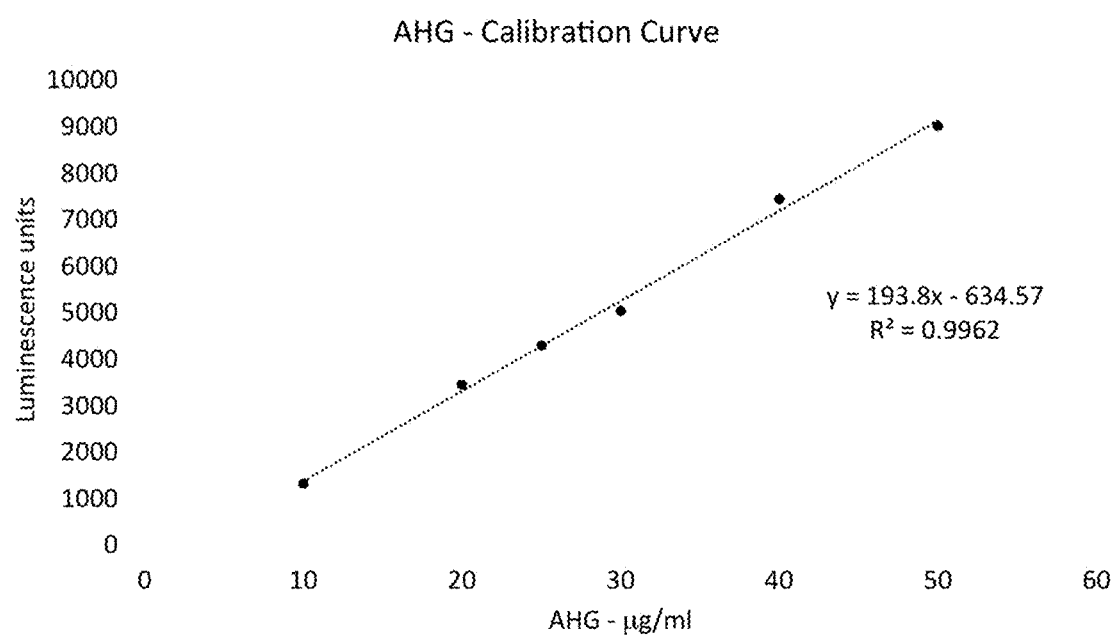
FIG. 27 illustrates a graph of standard curve of 1,5 AHG assay.

Example 13: Full Method of 1,5-AHG Measurements with Chemiluminescent Substrate Reaction buffer are prepared as following: 0.4 mL of 56.13 mg/mL $MgCl_2$, 0.6 mL of 66.13 mg/mL ATP, 0.7 mL distilled water are added to 8.4 mL of 75 mM TRIS-HCl pH 9. 80 uL of this reaction buffer are added to 10 uL of 1,5 AHG and 25 uL of water. The reaction buffer with 1,5 AHG is mixed with 35 uL of HRP, 75 uL of luminol and 60 uL of pyranose oxidase, and luminescent signal is read for 20 min. The correspondent light kinetics curve and calibration curve are shown in FIG. 26 and FIG. 27, respectively.

Example 14: Detection of Creatine

Creatine is naturally produced in the human body which as a high-energy reservoir for the rapid regeneration of ATP for all cells in the body, but mostly in muscle. Creatine supplementation also has been used as sports performance enhancer. Creatine is being studied as treatment for chronic congestive heart failure, neuromuscular and neurometabolic disorders. Quantification of creatine level in various body fluids is important and has extensive applications.

In this example, the enzymatic method involves the conversion of creatine to sarcosine with the aid of creatinase, and from sarcosine to glycine with enzyme sarcosine oxidase. The latter reaction releases hydrogen peroxide. The liberated hydrogen peroxide reacts with luminol with the aid of peroxidase to generate light. The emitted photons from the chemiluminescent reaction are detected using with POC detector device (shown in FIG. 32).

creatine+H₂O+creatinase=>sarcosine+urea sarcosine+O₂+H₂O+sarcosine oxidase=>glycine+ formaldehyde+H₂O₂

H₂O₂+luminol+peroxidase=>H₂O+light

In another modification, after reaction with sarcosine oxidase to produce hydrogen peroxide, 30 µL of luminol solution and 1 µg/mL laccase are added to the solution. With laccase as a catalyst, hydrogen peroxide reacts with luminol and emits light. Light intensity is measured using the point-of-care (POC) photon detector to quantify the creatine level.

In another modification of this application, after reaction with sarcosine oxidase, 30 µL of luminol solution and nanoparticles, such as silver nanoparticles, gold nanoparticles, platinum nanoparticles, iron oxide nanoparticles, nanoporous metal particles, or other metal catalysts, are added to the sample, hydrogen peroxide from the first reaction react with luminol in the presence of nanoparticles to thereby giving light. The light intensity is measure using the point-of-care (POC) photon detector.

In another example of this application after reaction with sarcosine oxidase, aryl oxalate such as diphenyl oxalate and a fluorescent substance is added to the sample, hydrogen peroxide from the first reaction react with aryl oxalate in the presence of a fluorescent substance to thereby excite the fluorescent substance, thus giving light. The light intensity is measure using the point-of-care (POC) photon detector.

Example 15: Dual Detection of Glucose and AHG

Figure 28:
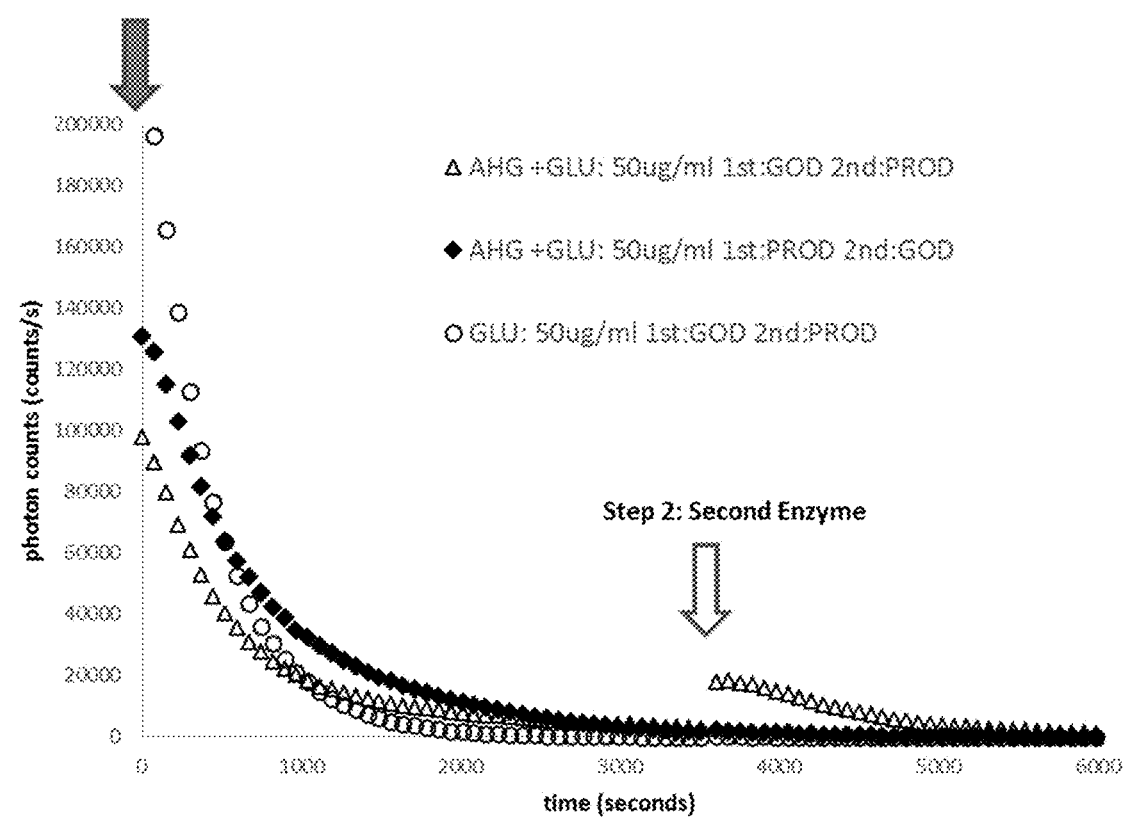
FIG. 28 illustrates a graph of feasibility of dual detection of glucose and 1,5-anhydroglucitol with two-step enzymatic reaction.

In FIG. 28, two identical samples containing 50 ug/ml of 1,5-anhydroglucitol and 50 ug/ml glucose, and a third sample containing only 50 ug/ml of glucose were used to test the feasibility of dual detection of glucose and 1,5-anhydroglucitol. In the first step, one of the two identical samples (sample 1, (hollow triangle marker)) and the glucose only sample (sample 3, (hollow circle marker)) were treated with glucose oxidase (GOD) while the other (sample 2, (solid diamond marker)) was treated with pyranose oxidase (PROD). Horseradish peroxidase and chemiluminescent substrate containing luminol was added to all samples and immediate followed by light measurement using photon detector. Once the light signals of all the samples reached the baseline, the second enzyme was added. Pyranose oxidase was added to the sample 1 (hollow triangle marker) and sample 3 (hollow circle marker) which were first treated with glucose oxidase. Glucose oxidase was added to sample 2 (solid diamond marker) which was first treated with pyranose oxidase. The second light measurement were done for all samples.

Figure 29:
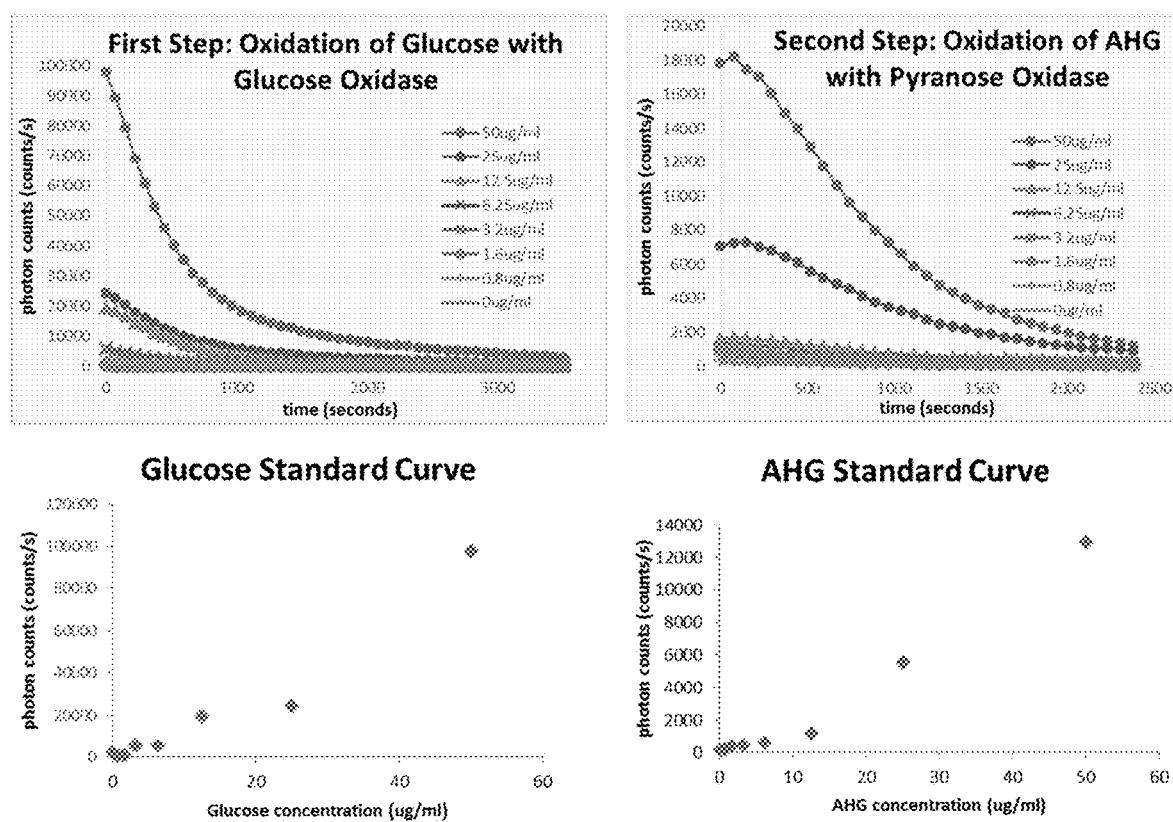
FIG. 29 illustrates graphs of dual detection of glucose and 1,5-anhydroglucitol with a two-step enzymatic reaction.

FIG. 29 illustrates a 2× dilution series of samples starting at 50 ug/ml of 1,5-anhydroglucitol and 50 ug/ml glucose. Two-step enzymatic reactions with dual light signal readout were carried out for all samples. Mixture of glucose oxidase and chemiluminescent substrate containing luminol was first added to the samples then immediately followed by light readout (top left). The results were used to create the glucose standard curve (bottom left). Once the light signals of all the samples reached the baseline, the pyranose oxidase was added. The second light measurement were done for all samples (top right). The results were used to create the 1,5-anhydroglucitol standard curve (bottom right).

Figure 30:
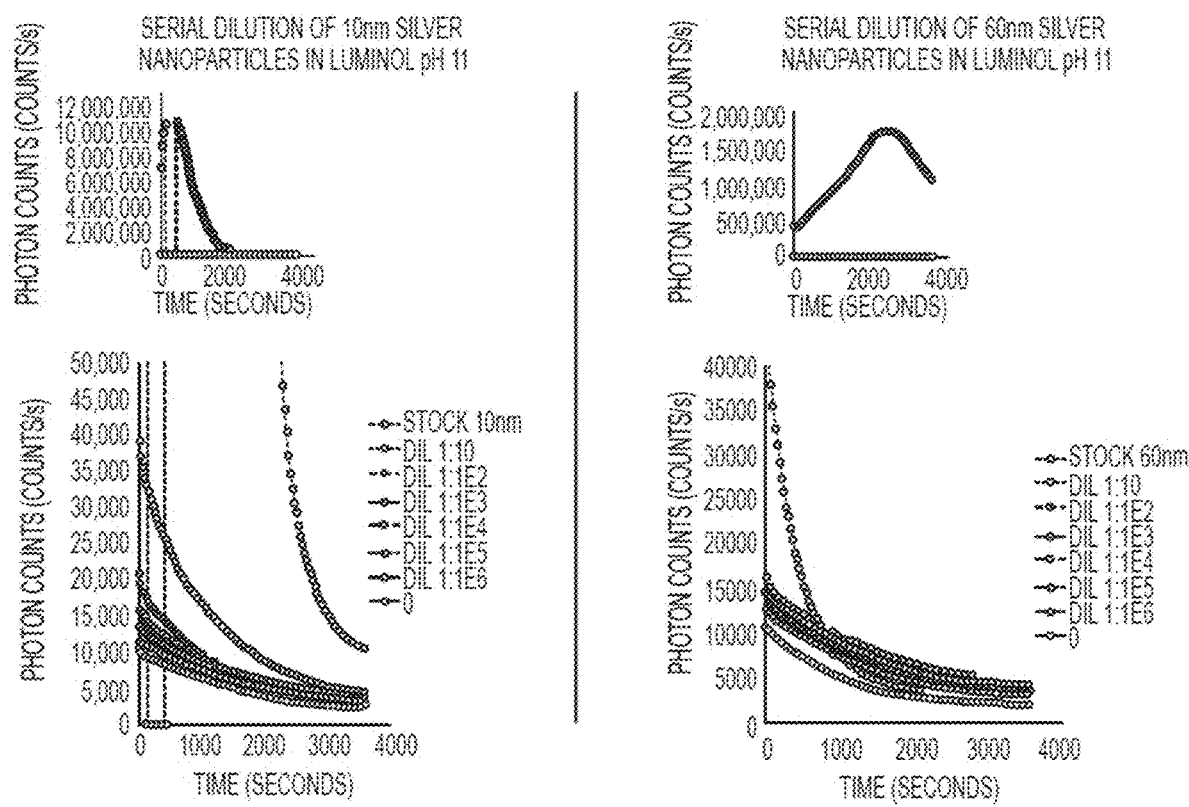
FIG. 30 illustrates graphs of photon counts of silver nanoparticles in a catalyzed chemiluminescent reaction.

In FIG. 30, 10 nm and 60 nm silver nanoparticles were used as the catalyst for chemiluminescent reaction. Chemiluminescent substrate containing luminol and hydrogen peroxide at pH 11 was added to the 10× dilution series of 10 nm and 60 nm silver nanoparticles. Top graphs have the y-axis at full range. Bottom graphs show zoomed-in scale of the y-axis for the low signal samples.

Figure 31:
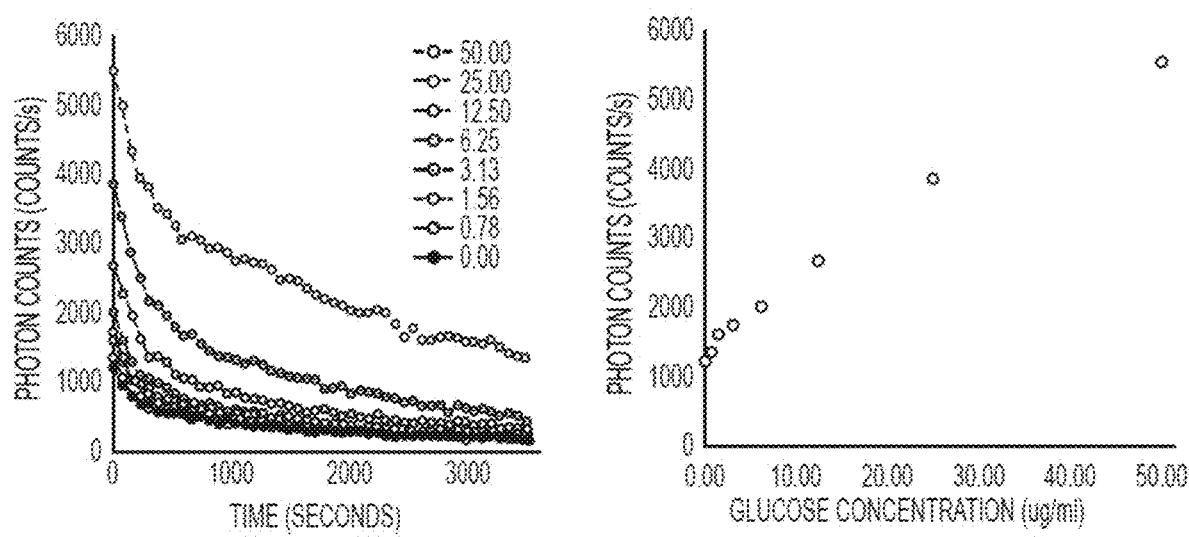
FIG. 31 illustrates a graph of the detection of glucose using silver nanoparticles as a catalyst in chemiluminescent reaction.

In FIG. 31, 10 nm silver nanoparticles were used in an assay to detect glucose. A 2× serial dilution of glucose solution, starting from 50 ug/ml, was mixed with glucose oxidase, silver nanoparticles, and chemiluminescent substrate containing luminol at pH 11. The samples were immediately measured using PMT for one hour (left). The first data points of each dilution were used to create the standard curve (right).

Example 16: Detection of Creatinine

Creatinine is produced from creatine, phosphocreatine and ATP as a result of muscle metabolic processes. It is excreted mainly by glomerular filtration during normal renal function. Thus, creatinine is important indicator of renal health. Creatinine assays are conducted for diagnostic purposes, for therapeutic monitoring of acute and chronic renal diseases, and for monitoring kidney dialysis.

Numerous methods have been described for determining creatinine. The enzymatic method is based on the established determination of hydrogen peroxide after conversion of creatinine with the aid of creatininase (creatinine amidohydrolase), creatinase, and sarcosine oxidase. The liberated hydrogen peroxide reacts with luminol with the aid of peroxidase to generate light. The emitted photons from the chemiluminescent reaction are detected using with POC detector device.

creatinine+H₂O creatininase=>creatine creatine+H₂O+creatinase=>sarcosine+urea sarcosine+O₂+H₂O+sarcosine oxidase=>glycine+ formaldehyde+H₂O₂

H₂O₂+luminol+peroxidase=>H₂O+light

Figure 32:
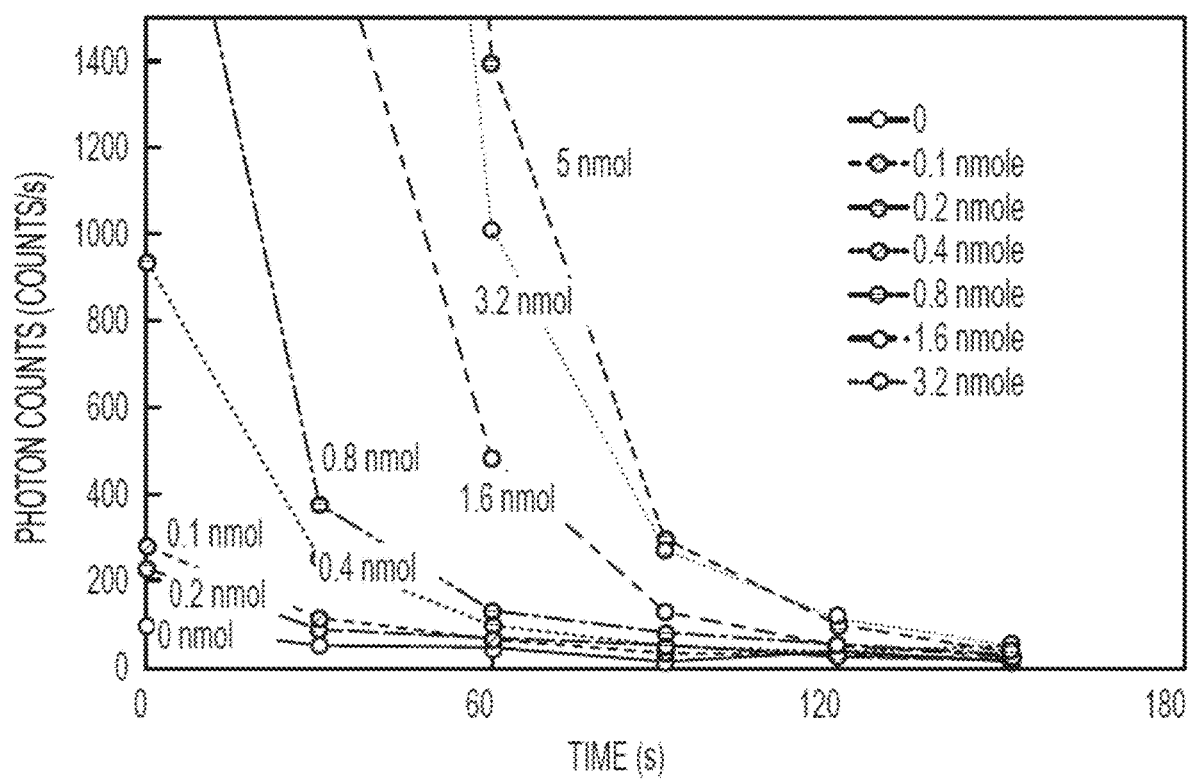
FIG. 32 illustrates a graph of the detection of creatinine with chemiluminescent substrate.
Figure 33:
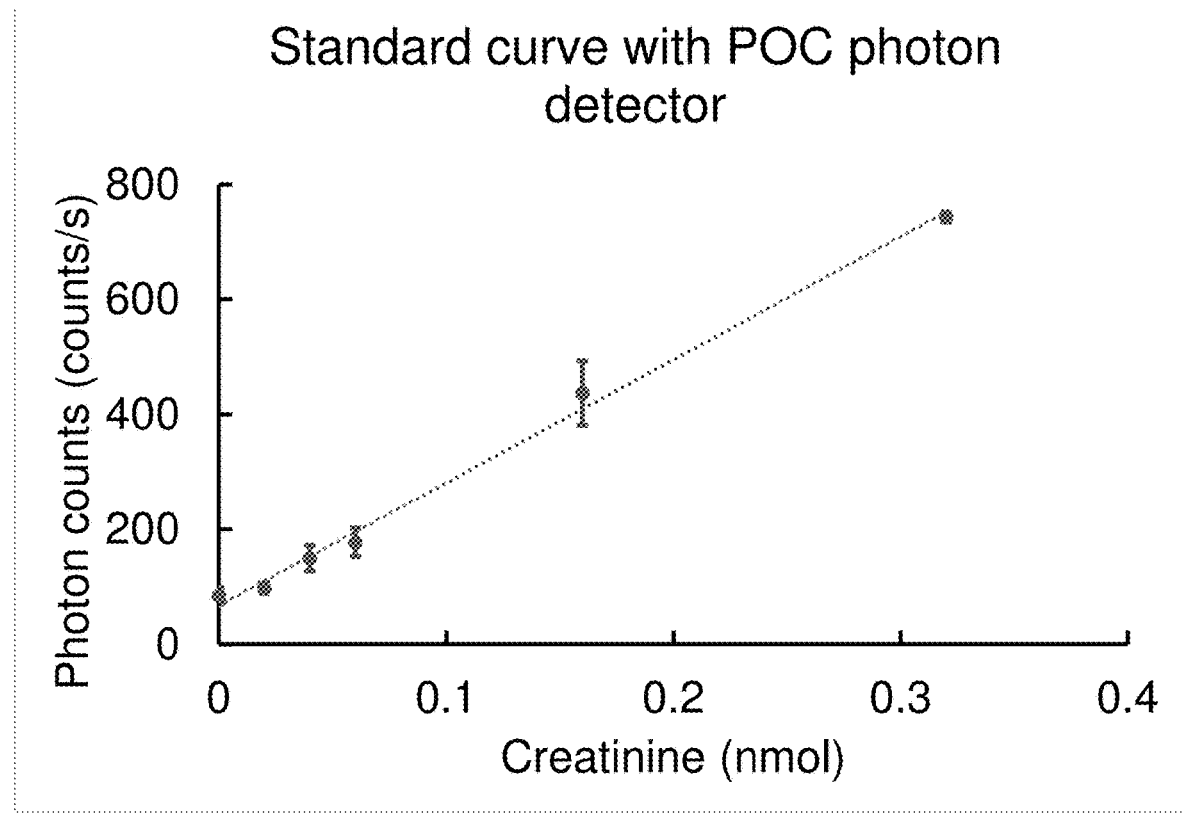
FIG. 33 illustrates a graph of a standard curve of a creatinine chemiluminescent assay with a point-of-care photon detector.

In this example, creatinine is first converted to creatine by enzyme creatininase. Then creatine is enzymatically converted of creatinine to sarcosine with the aid of creatinase, and from sarcosine to glycine with enzyme sarcosine oxidase. The latter reaction releases hydrogen peroxide. The liberated hydrogen peroxide reacts with luminol with the aid of peroxidase to generate light. FIG. 32 illustrates the detection of creatinine with a chemiluminescent substrate. The emitted photons from the chemiluminescent reaction are detected using with POC detector device (shown in FIG. 33).

In another modification, after reaction with sarcosine oxidase to produce hydrogen peroxide, 30 µL of luminol solution and 1 µg/mL laccase are added to the solution. With laccase as a catalyst, hydrogen peroxide reacts with luminol and emits light. Light intensity is measured using the point-of-care (POC) photon detector to quantify the creatinine level.

In another modification of this application, after reaction with sarcosine oxidase, 30 µL of luminol solution and nanoparticles, such as silver nanoparticles, gold nanoparticles, platinum nanoparticles, iron oxide nanoparticles, nanoporous metal particles, or other metal catalysts, are added to the sample, hydrogen peroxide from the first reaction react with luminol in the presence of nanoparticles to thereby giving light. The light intensity is measure using the point-of-care (POC) photon detector.

In another example of this application after reaction with sarcosine oxidase, aryl oxalate such as diphenyl oxalate and a fluorescent substance is added to the sample, hydrogen peroxide from the first reaction react with aryl oxalate in the presence of a fluorescent substance to thereby excite the fluorescent substance, thus giving light. The light intensity is measure using the point-of-care (POC) photon detector.

Example 17: Detection of Urea

Urea plays an important role in human metabolic system. It functions as the transporter for nitrogen waste from protein metabolism to the kidneys and then excreted in urine. Urea also plays a role in the exchange system of the nephrons to re-absorb water and critical ions from the excreted urine. Urea is an excellent indicator of renal health. Therefore, urea measurement is a routine diagnostic procedure, and there are numerous different colorimetric methods available.

In this example, we describe an enzymatic chemiluminescent method. Urea is first hydrolyzed to ammonia by enzyme urease. Ammonia reacts with glutamate and ATP in the presence of glutamine synthetase and produce ADP. ADP is measured in reactions catalyzed successively by pyruvate kinase and then by pyruvate oxidase in a system that generates hydrogen peroxide. The liberated hydrogen peroxide reacts with luminol with the aid of peroxidase to generate light. The emitted photons from the chemiluminescent reaction are detected using with POC detector device.

Urea+$H_2O$+urease(EC 3.5.1.5)=>$CO_2$+2$NH_3$

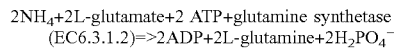
2$NH_4$+2L-glutamate+2 ATP+glutamine synthetase (EC6.3.1.2)=>2ADP+2L-glutamine+2$H_2PO_4^-$

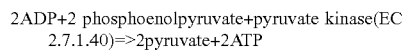
2ADP+2 phosphoenolpyruvate+pyruvate kinase(EC 2.7.1.40)=>2pyruvate+2ATP

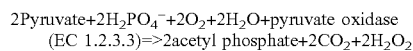
2Pyruvate+2$H_2PO_4^-$+2$O_2$+2$H_2O$+pyruvate oxidase (EC 1.2.3.3)=>2acetyl phosphate+2$CO_2$+2$H_2O_2$

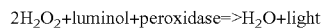
2$H_2O_2$+luminol+peroxidase=>$H_2O$+light

In another modification, after reaction with pyruvate oxidase to produce hydrogen peroxide, 30 μL of luminol solution and 1 μg/mL laccase are added to the solution. With laccase as a catalyst, hydrogen peroxide reacts with luminol and emits light. Light intensity is measured using the point-of-care (POC) photon detector to quantify the urea level.

In another modification of this application, after reaction with pyruvate oxidase, 30 μL of luminol solution and nanoparticles, such as silver nanoparticles, gold nanoparticles, platinum nanoparticles, iron oxide nanoparticles, nanoporous metal particles, or other metal catalysts, are added to the sample, hydrogen peroxide from the first reaction react with luminol in the presence of nanoparticles to thereby giving light. The light intensity is measure using the point-of-care (POC) photon detector.

In another example of this application after reaction with pyruvate oxidase, aryl oxalate such as diphenyl oxalate and a fluorescent substance is added to the sample, hydrogen peroxide from the first reaction react with aryl oxalate in the presence of a fluorescent substance to thereby excite the fluorescent substance, thus giving light. The light intensity is measure using the point-of-care (POC) photon detector.

The methods described herein are further described by amplification of individual elements of embodiments of the methods. The utility of the exemplary embodiments of the present disclosure include fields such as Clinical Diagnosis; Prognosis, Pathogen discovery; Biodefense; Research; Adulterant Detection; Counterfeit Detection; Food Safety; Taxonomic Classification; Microbial ecology; Environmental Monitoring; Agronomy; and Law Enforcement.

Analytes:

In exemplary embodiments, an analyte of interest may include 1,5-anhydroglucitol, glucose, creatine, creatinine, urea, metabolites, a protein, a peptide, a hormone, a biomarker, a toxin, or a modified (e.g., phosphorylated or acetylated) protein.

Analytes Sources:

In exemplary embodiments, the specimen in which the analyte is to be detected may comprise a biopsy specimen, blood, serum, plasma, stool, saliva, sputum, CSF, lavage fluid, nasal wash, urine, cell lysate, drinking water, natural water, sea water, soil water, soil leachate, fresh tissue, frozen tissue, neutral formalin-treated tissue, formalin fixed paraffin embedded tissue block, or an ethanol-fixed paraffin-embedded tissue block.

Sample Pretreatment:

In exemplary embodiments, a specimen may be optionally pre-treated for concentration of the analyte, removal of particulates, contaminants, interferences, or reaction inhibitors, reduction of viscosity, improvement of handling properties, or to modify the analyte for improved detection. The methods to selectively remove or modify the interferences or contaminants include the uses of antibody capturing, aptamer capturing, enzymatic reactions, chemical modifications or chromatography techniques such as ion exchange, HIC, metal chelate, boronate, or affinity.

Reagents:

In exemplary embodiments, the readout method by which the analyte is detected may be the emission of light by chemiluminescence, bioluminescence, or any method may be used for generate the light signal in the method of the present invention. Reagents to generate light output are chemiluminescent substrates, such as luminol, isoluminol, 1,2-dioxetanes, peroxyoxalate compounds and dyes, or bioluminescent substrates, such as luciferin. The signal generation reaction can be generated with or without enzyme. Among the available methods, oxidization of various chemiluminescent substrates with hydrogen peroxide catalyzed by peroxidase is the most common. There are other known methods for detecting hydrogen peroxide through chemiluminescence without using peroxidase, for example, the luminescence can be obtained with luminol and hydrogen peroxide in the presence of laccase. Luminescence can also be obtained without enzyme by reacting luminol and hydrogen peroxide in the presence of a ferricyanide ion, by reacting lucigenin with hydrogen peroxide in the presence of a metal ion, by reacting an aryl oxalate such as bis(2,4,6-trichlorophenyl) oxalate with hydrogen peroxide in the presence of a fluorescent substance, and by reacting luminol and hydrogen peroxide in the present of silver nanoparticles or iron oxide nanoparticles, or silver catalyst.

Assaying Apparatus:

In exemplary embodiments, the assay may be done on a microfluidic device which comprises multiple functional aspects: separation or removal of interferences, reaction to generate signal, and optical signal readout areas. In additional embodiments, the microfluidic device may contain multiple separation/removal, reaction, and signal readout areas for multiplexing, where more than one analyte can be assessed. The separation area in microfluidic device contains adsorbent or absorbent to separate or remove interferences from analytes. In another embodiment, the separation area in microfluidic device contains enzyme to convert interferences to non-interferences. The apparatus can be made by 3D printer, injection mold, blow molding, extrusion molding, vacuum forming, compression molding or any other manufacturing techniques.

Detector Devices:

In exemplary embodiments, the luminescent signal output may be detected by a light detector such as, but not limited to, a charged coupled device (CCD), avalanche diode, (multi-pixel photon counter) MPPC or silicon photomultiplier (SiPMT), complementary metal-oxide-semiconductor (CMOS) sensor, scientific CMOS (sCMOS) sensor, photomultiplier tubes (PMT), photodiode, camera, cellphone camera, web camera, smart watch camera, or any light detector. The light detector can function as a point-of-care device connected and controlled via wired or wireless connection by personal computer, laptop, tablet, smart phone, smart watch, or any similar devices with computing and displaying capabilities. The wireless connection includes, but is not limited to, Bluetooth, Wi-Fi, and near field communication (NFC).

The assay can be done in plate format and signals are read out by a plate reader equipped with photomultiplier tubes (PMT), avalanche diode, (multi-pixel photon counter) MPPC or silicon photomultiplier (SiPMT), charged coupled device (CCD) sensor, complementary metal-oxide-semiconductor (CMOS) sensor, scientific CMOS (sCMOS) sensor.

Example 18: Clearing of Inhibitors for Chemiluminescent Assays

Figure 34:
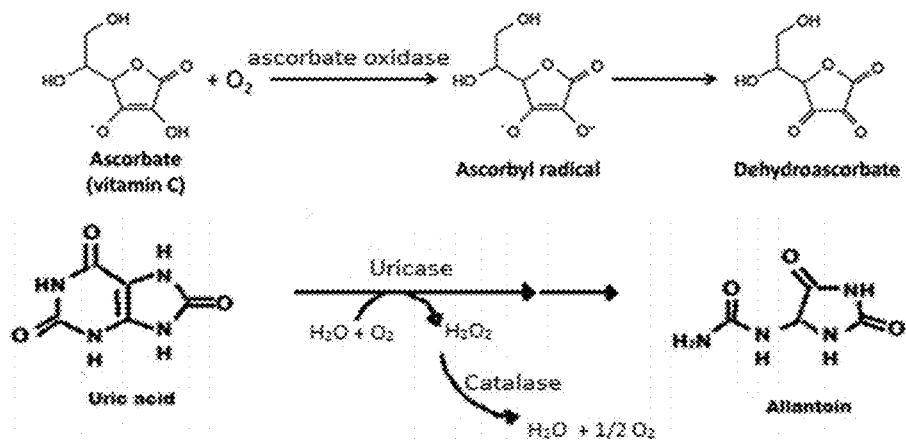
FIG. 34 illustrates a schematic of a chemiluminescent reaction involving saliva and enzymes including uricase and ascorbase.

Antioxidants are essential to the body's defense system. They neutralize free radicals, such as reactive oxygen species (ROS) that damage cells. The primary antioxidants in saliva include uric acid, ascorbic acid, albumin, glutathione and antioxidant enzymes. Their antioxidative activity can also interfere with a chemiluminescent reaction, which is an oxidation process. The presence of antioxidants in a chemiluminescent reaction can diminish or delay light signal output. In fact, the time delay of light signal is sometimes used to quantify the amount of antioxidants in the samples. The removal of these antioxidants is necessary for some chemiluminescent reactions, such as those using luminol based reagents. FIG. 34 illustrates a schematic of a chemiluminescent reaction involving saliva and enzymes including uricase and ascorbase.

In an example, before the chemiluminescent reaction, 500 ul of saliva is treated with 0.05 U of uricase, 0.05 U of ascorbase, polyphenol oxidase, glutathione oxidase and other enzymes then incubated for 10 minutes at 37 C to remove small antioxidants that inhibit the chemiluminescent reaction. Catalase is added to remove hydrogen peroxide produced from the oxidation of these antioxidants. The sample is then filtered with a 3 kD molecular weight cut-off (MWCO) filter to remove the bigger antioxidant molecules such as superoxide dismutases (SODs), as well as catalase, etc. Once cleared of antioxidants, the metabolites in the sample can be assayed with chemiluminescent reaction read out.

Specifically, we can measure glucose, galactose, and 1,5-anhydroglucitol (AHG) in one antioxidant-cleared sample. Antioxidant-cleared sample containing 1,5-anhydroglucitol is mixed with 10 µL of enzyme mix containing glucose oxidase, peroxidase and chemiluminescent substrate, then immediately followed by light intensity measurement using the photon detector. The light signal is interpreted as glucose concentration. After the first reaction is completed, galactose oxidase is added then immediately followed by light intensity measurement using the high sensitivity light detector. The signal is interpreted as galactose concentration. Finally, pyranose oxidase is added, then immediately followed by light intensity measurement using the photon detector. The signal is interpreted as AHG concentration. The ratio of 1,5-anhydroglucitol to glucose or galactose can be used to correct for the variations in sample collection.

In a modification, after 10 minutes incubation at 37 C with enzymes to remove antioxidants, the sample is heated at 95 C for 10 minutes to inactivate all the enzymes and other macromolecule antioxidants such as superoxide dismutases (SODs), catalase, etc. Once clear of antioxidants, the metabolites in the sample can be assayed with chemiluminescent reaction read out.

In another modification, before the chemiluminescent reaction, 500 ul of saliva is treated with 0.05 U of uricase, 0.05 U of ascorbase, glucose oxidase, galactose oxidase, polyphenol oxidase, glutathione oxidase and other enzymes to remove small antioxidants that inhibit the chemiluminescent reaction and to remove interferents in the AHG reaction. Catalase is also added to remove hydrogen peroxide produced from the oxidation of these antioxidants. The sample is incubated at 37 C for 1 to 90 minutes, typically, 10 minutes. The sample is then filtered or heated to remove or inactivate the bigger antioxidant molecules such as superoxide dismutases (SODs), catalase, etc. Once clear of antioxidants and interferents, the AHG in the sample can be assayed with chemiluminescent reaction read out. Antioxidant and interferents cleared sample containing 1,5-anhydroglucitol is mixed with 10 µL of enzyme mix containing pyranose oxidase, peroxidase and chemiluminescent substrate, then immediately followed by light intensity measurement using the photon detector. The light signal is interpreted as AHG concentration.

In another example, before the chemiluminescent reaction, 500 ul of saliva sample is filtered or heated to remove or inactivate the bigger antioxidant molecules such as superoxide dismutases (SODs), catalase-like enzymes, etc. Saliva is then treated with 0.05 U of uricase, 0.05 U of ascorbase, and other enzymes and incubated for 10 minutes at 37 C to convert small antioxidants that inhibit the chemiluminescent reaction to hydrogen peroxide. The hydrogen peroxide produced from the oxidation of these antioxidants is quantified by chemiluminescent reaction with HRP and luminol substrate. The signal can be used to normalize other measurements for dilution by saliva production. Once cleared of antioxidants, the sample can be assayed with conventional chemiluminescent reaction read out.

In a modification, the treated sample is urine. It is known that urine contains high level of uric acid. Removal of uric acid and other antioxidants is necessary in assays using luminol based chemiluminescent substrate. In another modification, the sample treated with the enzyme mix is blood, which contains catalase and other antioxidants. In another modification, the peroxidase is derived from sweet potato, or in a preferred modification, from soybean.

Alternatives to Luminol Chemistry

The presence of antioxidants in bodily fluids makes sensitive luminol based chemiluminescent assay unreliable without any pretreatment. The presence of antioxidants in chemiluminescent reaction can diminish or delay light signal output. Among the chemiluminescent methods to detect hydrogen peroxide, peroxyoxalate chemistry and acridinium ester chemistry are impervious to antioxidant interference.

Peroxyoxalate Chemistry Detection Method

Figure 35:
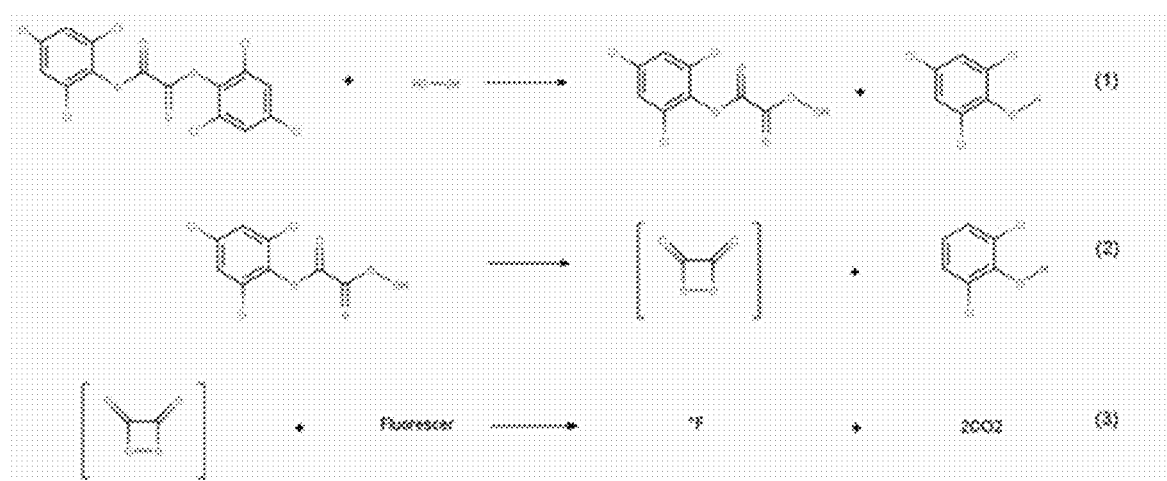
FIG. 35 illustrates a schematic of a chemical reaction is in which bis(2,4,6-trichlorophenyl) oxalate TCPO is dissolved in ethyl acetate.
Figure 36:
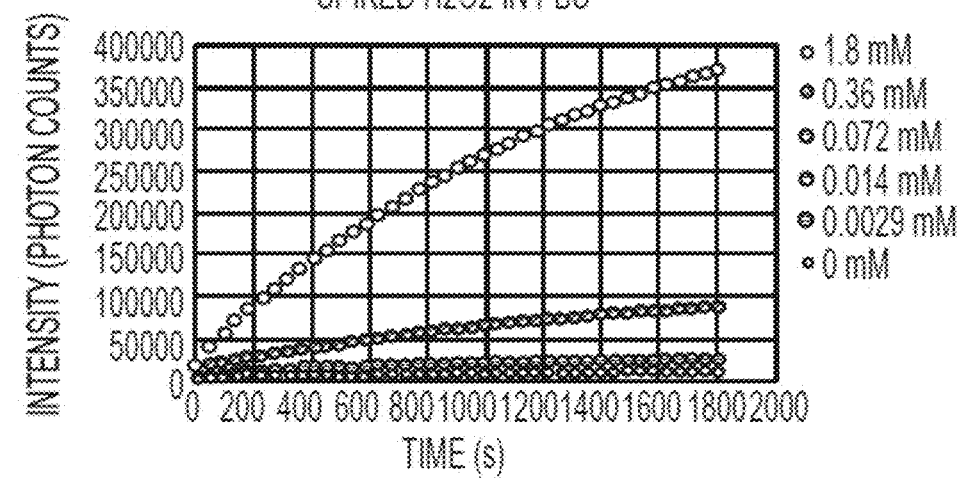
FIG. 36 illustrates graphs demonstrating the compatibility of peroxyoxalate chemistry with saliva for hydrogen peroxide detection.
Figure 36:
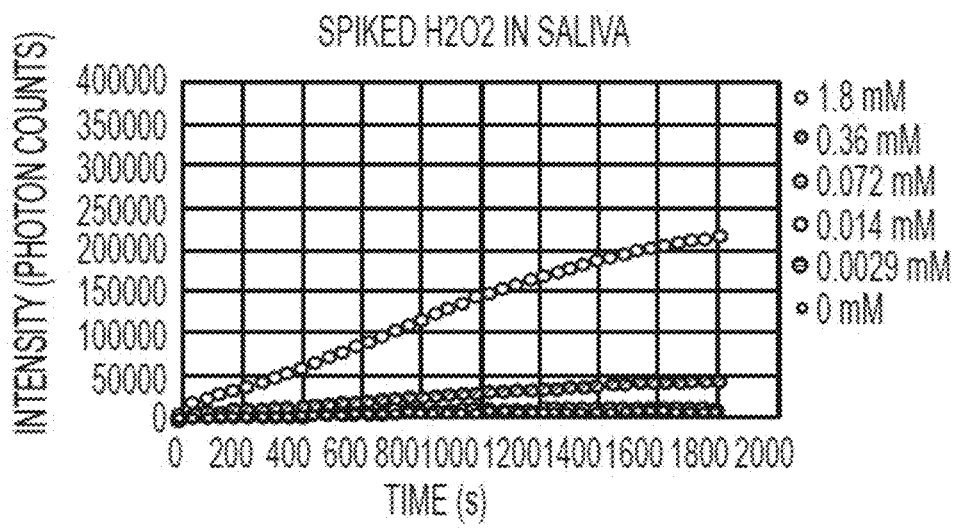

An example of substrate of peroxyoxalate chemistry is bis(2,4,6-trichlorophenyl) oxalate (TCPO) which is used in glowsticks. Other variations of TCPO molecule have been synthesized for solvent compatibility and also can be used. Referring now to FIG. 35, a schematic of a chemical reaction is shown in which TCPO is dissolved in ethyl acetate to 600 mg/l. Graphs demonstrating the compatibility of peroxyoxalate chemistry with saliva for hydrogen peroxide detection are shown in FIG. 36. The graph on the left illustrates the response of hydrogen peroxide in phosphate-buffered saline (PBS) and the graph on the right illustrates the response of hydrogen peroxide in saliva.

A fluorescer such as perylene is added at a concentration of 50 mg/l. The fluorescer can be chosen to spectrally match to the spectral sensitivity of an electronic detector to be used. A small amount of base catalyst, trimethylamine (50 ul/l) is added to make the chemiluminescent substrate. This TCPO substrate can be used to detect metabolites or other compounds in samples such as saliva, urine, blood, food, beverages, or natural or process waters. For example, a sample containing 1,5-anhydroglucitol is mixed with 10 μL of enzyme mix containing glucose oxidase and TCPO chemiluminescent substrate, then immediately followed by light intensity measurement using the point-of-care (POC) photon detector. The light signal is interpreted as glucose concentration. After the first reaction completed, galactose oxidase is added then immediately followed by light intensity measurement for galactose signal. Finally, pyranose oxidase is added then immediately followed by light intensity measurement using the high sensitivity light detector. The signal is interpreted as 1,5-anhydroglucitol concentration. The ratio of 1,5-anhydroglucitol to glucose can be used to correct for the variations in sample collection method.

Liquid Waveguide Capillary Cell

In spectroscopy, the sensitivity of most methods is directly proportional to the optical path length of the sample holder. Increasing the path length using a conventional sample cuvette requires a bigger sample volume which is not always possible. Furthermore, the additional space to accommodate the sample holder is a constraint. A liquid waveguide capillary cell solves this problem by making the sample become the flexible light conduit. the liquid waveguide capillary cell is based on the total internal reflection, concept similar to that which allows optical fibers to transmit light along their flexible length. In an optical fiber, a high refractive index core is surrounded by lower refractive index material. A light ray which enters in fiber at an angle greater than the critical angle to the normal will be internally reflected and transmitted along the fibers length. In a liquid waveguide capillary cell, the liquid serves as the high refractive index core and the tube wall serves the low refractive index cladding. For aqueous applications, water has very low refractive index (1.33) thus the availability of suitable cladding materials is very limited, and those that have been demonstrated are very expensive. DuPont's Teflon AF 1600 and Teflon AF 2400 have refractive indices of 1.31 and 1.29, respectively, and are currently used for cladding material in liquid waveguide capillary cell.

Moderately low refractive index materials are much less expensive, such as fluorinated ethylene propylene (FEP). FEP is widely used as transparent tubing with refractive index of 1.341-1.347, which is higher than that of water. Using FEP as the cladding material for aqueous liquid waveguide capillary cell is not possible due to its high refractive index relative to water. In a modification, we solve this problem by modifying the aqueous liquid core with high refractive index substances to make its refractive index higher than that of the inexpensive tubing.

Modification of Core Index of Refraction

The refractive of the core liquid can be increased with the addition of salts such as calcium chloride, sugars such as sucrose, or substances with high refractive index (increment) such as glycerol.

In an example, the aqueous liquid to be analyzed is mixed with glycerol (10% to 90%, typically 20%) to give a solution with refractive index greater than that of the FEP tubing. The solution then is injected into the tube with preselected path length. The injection method is designed to be free or nearly free of air bubbles. Elevated pressure can be applied to the core liquid to force the air bubbles to shrink and dissolve into the liquid. Once free of bubbles, the liquid core has the ability to guide the light and the measurement or readout can be performed.

In another example, the aqueous liquid to be analyzed is mixed with sucrose (10% to 90%, typically 20%) to make the refractive index of the solution greater than that of the FEP tubing. The solution then is injected into a tube with preselected path length. The injection method is designed to be free of or to have minimal air bubbles. High pressure can be applied to the core liquid to force the air bubbles to shrink and dissolve into the liquid. Once free of bubbles, the liquid core has the ability to guide the light and the measurement or readout can be performed.

In another example, calcium chloride (CaCl2) is added to the aqueous liquid to be analyzed to increase the refractive index of the solution. The solution then is injected into an FEP tube with preselected path length of 70 cm. The liquid core has the ability to guide the light and the measurement or readout can be performed.

Different Formats of Liquid Waveguide Capillary Cell

In an example, the liquid waveguide capillary cell is comprised of FEP tubing with internal diameter from 0.1 mm to 1 mm. The FEP tubing is arranged in a coil with diameter greater than the minimum bend radius to maintain the proper wave guiding operation and mechanical stability. The length of the tubing determines its optical path length and thus its sensitivity. The ends of the tubing are terminated by T-adapters which allow light to enter and exit along the axial direction of the tubing and liquid to flow in and out from the lateral direction. The T-adapters can be interfaced with optical fibers that can be connected to light source and detector.

In another example, the liquid waveguide capillary cell is composed of a fluidic cartridge fabricated with FEP plastic by injection molding, hot embossing, 3-D printing, or other plastic manufacturing processes. The fabricated liquid waveguide capillary cell can be straight, curved, or coiled depending on the path length, the space constraints and minimum bend radius. The ends of the liquid waveguide capillary cell are terminated by T-format which allow light to enter and exit along the axial direction of the tubing and liquid to flow in and out from the lateral direction. One end can be interfaced with light source and the other end to the detector.

Absorbance Measurement with Liquid Waveguide Capillary Cell

In typical colorimetry measurements, the standard path length is 1 cm. According to the Beer-Lambert law, the sensitivity of the measurement is directly proportional to the path length, but a longer path length would require a large sample volume which not always available. Furthermore, the path length needs to be perfectly straight, and so a longer path length would require precision manufacturing process and would be bulky. In contrast, the liquid waveguide capillary cell can have a very long path length and requires a very low sample volume. For the same volume, the path length of liquid waveguide capillary cell can be 100 times longer than the conventional curvet. The liquid waveguide capillary cell can be curved or coiled to save space.

In an example, AHG level in saliva can be detected with colorimetry using a liquid waveguide capillary cell. After the removal of all interferents, pyranose oxidase is be added to the sample to convert AHG to hydrogen peroxide. TMB substrate and horseradish peroxidase then are added to the sample and incubated for 30 min. The reaction is then stopped with 0.16M sulfuric acid followed by the addition of a refractive index modifier such as calcium chloride, glycerol, or others to increase the refractive index to be greater than that of the tubing. The sample then is injected into the FEP tube with preselected path length. An absorbance measurement can be performed by transmitting the light from one terminal and analyzing on the other terminal.

In another modification, hydrogen peroxide can be detected by adding ammonium titanyl oxalate to the sample followed by the addition of a refractive index modifier such as calcium chloride, glycerol, or others to increase the refractive index to greater than that of the tubing. The sample then is injected into the FEP tube with 50 cm path length for absorbance measurement.

Figure 37:
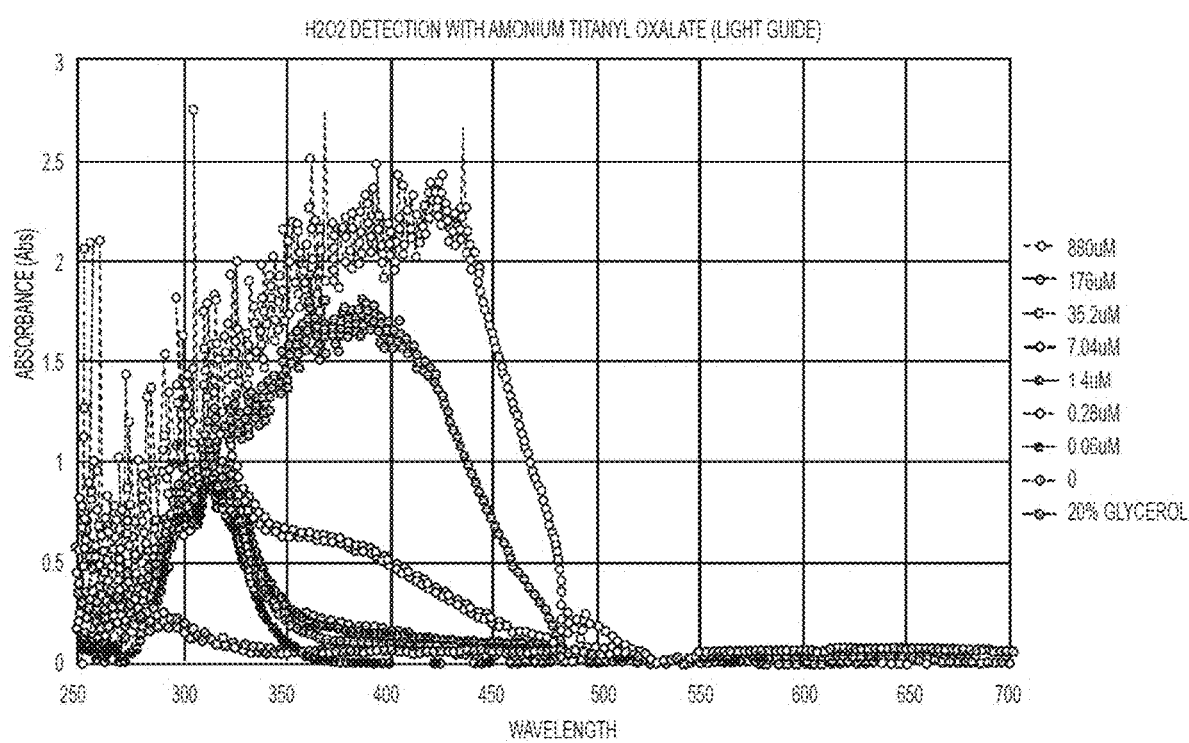
FIG. 37 illustrates a graph of hydrogen peroxide detection with ammonium titanyl oxalate.

Results of the hydrogen peroxide detection with ammonium titanyl oxalate described above are shown in FIG. 37.

Concentration of total bilirubin (the sum of unconjugated and conjugated bilirubin) in plasma, total hemoglobin, oxygen saturation, fraction of oxyhemoglobin, carboxyhemoglobin, deoxyhemoglobin, methemoglobin, and fetal hemoglobin can be measured using liquid waveguide cell. For example, the whole blood sample is hemolyzed and diluted with plasma and mixed with refractive index modifier such as glycerol, CaCl2 and others to increase the refractive index to greater than that of the tubing. The mixture is transported to the liquid waveguide cell. The injection method is designed to be free of or to have minimal air bubbles. High pressure can be applied to the core liquid to force the air bubbles to shrink and dissolve into the liquid. The temperature of the liquid waveguide cell is regulated to 37 C. Light is sent to one end of the liquid waveguide cell. The light transmitted through the liquid waveguide cell is guided to the spectrometer. The absorption spectrum of the sample is used to calculate the oximetry parameter values. From these spectral data, bilirubin was calculated together with oximetry values (hemoglobin, fetal hemoglobin, oxygen saturation, and others) and is adjusted for the presence of hemoglobin, fetal hemoglobin, and other matrix components.

Chemiluminescent Measurement with Liquid Wave Guide Capillary Cell

The sensitivity of chemiluminescent detection depends on the ability to collect the light signal from the reaction volume. The collection optics need to be as close as possible to the light-emitting sample due to the inverse-square relationship between the intensity and distance. Collecting emitting light from a large sample volume is difficult and not efficient. The liquid waveguide capillary cell can effectively collect light along its length and transmit to the light to the detector with no or very few optical elements.

In an example, AHG level in saliva can be detected with a chemiluminescent method using a liquid waveguide capillary cell. After the removal of interferents, pyranose oxidase is added to the sample to convert AHG to hydrogen peroxide. Chemiluminescence substrate and horseradish peroxidase then are added to the sample and followed by the addition of a refractive index modifier such as calcium chloride, glycerol, or others to increase the refractive index to greater than the that of the tubing. The sample then is injected into the FEP tubing. The injection method is designed to be free of any air bubbles. Light is detected at the one or both ends of the tubing.

Fluorescence Measurement with Liquid Waveguide Capillary Cell

Another application for liquid waveguide capillary cell is for fluorescence measurement. Fluorescent analyte in the sample can be excited by a light source introduced along the axial length of the liquid waveguide capillary cell, using e.g., a semi-silvered mirror, or laterally through the wall. A fraction of the emitting light is collected and transmitted along the liquid waveguide capillary cell to the ends. The light signal can be filtered and measured with a light detector.

In an example, the AHG level in saliva can be detected with fluorescence measurement method using a liquid waveguide capillary cell. After the removal of all interferents, a refractive index modifier such as calcium chloride, glycerol, and others to increase the refractive index to greater than that of the tubing is added to the sample. Pyranose oxidase is then added to the sample to convert AHG to hydrogen peroxide. Amplex red substrate and horseradish peroxidase then are added to the sample and the sample then is injected into the FEP tubing and allowed to incubate at 37 C for 10 min. Amplex red is oxidized to resorufin, a highly colored and fluorescent compound. The tube is exposed to light at excitation wavelength, 538 nm. Light is filtered and detected at the one or both ends of the tubing at 587 nm for measurement of AHG.

Raman Spectroscopy with Liquid Waveguide Capillary Cell

Raman spectroscopy can be used to identify and quantify target molecules in a sample by observing the vibrational, rotational, and other low-frequency modes. A monochromatic light, usually from a laser, interacts with molecular vibrations, or other excitations in the system, causing in the energy of the laser light being shifted up and down. The shift in the wavelength and the intensity of the emitting light give information about identity and the quantity of the target analytes. The intensity of the Raman signal is very weak and thus requires very long excitation path length. Liquid waveguide capillary cell can be used to enhance Raman signal. The sample can be excited along the tube by injecting monochromatic light from one end of tube and the signal can be filtered and analyzed on the other end. The surface of the waveguide can be modified to enhance Raman signals. Signals can be interpreted using deep learning or neural network algorithms.

Immunoassay in Liquid Waveguide Capillary Cells

Immunoassay such as enzyme-linked immunosorbent assay (ELISA) can be performed in liquid waveguide capillary cells for detecting and quantifying substances such as peptides, proteins, antibodies, hormones, metabolites, or toxins. The inner surface of the liquid waveguide capillary cells can be functionalized with molecular recognition element such as an antibody, aptamer, nucleic acid, antibody analog, lectin, receptor, hormone, toxin, or drug or drug analog. The functionalization can be done with passive adsorption or covalent chemical modification. The immobilized molecular recognition element is used to capture the target molecules. For large target molecules such as protein, sandwich assay format can be used performed using enzyme-linked molecular recognition element for detection (direct method) or using a primary molecular recognition element to bind to the target then followed by an enzyme-linked secondary molecular recognition element that recognizes the primary recognition element for detection (indirect method). After washing followed by addition of substrate, the bound conjugated enzyme will convert the substrate to measurable product. For small target molecules such as metabolites, competitive assay can be performed using labeled antigen. Unlabeled antigen from samples and the labeled antigen compete for binding to the capture molecular recognition element. A decrease in signal from labeled antigen indicates the presence of the antigen in samples when compared to assay wells with labeled antigen alone.

In an example, 1,5-anhydroglucitol (AHG) in saliva can be assayed with immunoassay method in liquid waveguide capillary cell. This assay employs the competitive enzyme immunoassay technique. A monoclonal antibody specific to AHG has been pre-coated onto the inner surface of 50 cm long FEP liquid waveguide capillary cell. A competitive reaction is performed between biotin labeled AHG and unlabeled AHG in the samples with the pre-coated antibody specific to AHG. After incubation the unbound conjugate is washed off. Next, avidin conjugated to Horseradish Peroxidase (HRP) is added to liquid waveguide capillary cell and incubated. After a number of flow thru with wash buffer, the substrate such as TMB and refractive index modifier is pump in the liquid waveguide capillary cell. The amount of bound HRP conjugate is reverse proportional to the concentration of AHG in the sample. The intensity of color developed is reverse proportional to the concentration of AHG in the sample. An absorbance measurement can be performed by transmitting the light from one terminal and analyzing on the other terminal. The absorbance value can be compared with the standard to determine the AHG concentration in the sample.

In a modification, after adding avidin conjugated to Horseradish Peroxidase (HRP), Amplex red substrate is used as the substrate instead of TMB. Amplex red is oxidized to resorufin, a highly colored and fluorescent compound. The tube is exposed to light at excitation wavelength, 538 nm. Light is filtered and detected at the one or both ends of the tubing at 587 nm for measurement of AHG.

Non-Aqueous Applications:

Many non-aqueous liquids have refractive index higher than that of FEP tubing. This allows the application of liquid waveguide capillary cell to quantitatively and qualitatively measure these substances or substances in them without any modification to the sample.

In an example, liquid waveguide capillary cell is used to check the authenticity, purity and the adulteration of olive oil. An oil sample is injected into the liquid waveguide capillary cell. Since the liquid core has the higher refractive index than the tubing, it has ability to guide the light. The absorbance measurement can be performed by transmitting the light from one end and analyzing on the other terminal, or by using a mirror at one end and a semi-silvered T format coupler and light source and detector at the other. The spectral result is checked against the standard to determine its authenticity, purity and the adulteration.

Enzyme reactions in non-aqueous media can be used for bioanalysis in liquid waveguide capillary cells, e.g. in flow injection analysis mode (see Anal. Chem., 1992, 64 (2), pp 129-133). In an example, the first half of the length of a liquid waveguide cell is packed with controlled-pore glass bearing immobilized cholesterol oxidase and soybean peroxidase. Toluene samples containing cholesterol and spiked with p-anisidine substrate are flowed through the capillary, and cholesterol concentration is inferred from absorbance measurements conducted along the second half of the capillary.

Sample Preparation and Pre-Concentration

When the target molecule is a low molecular weight monosaccharide, it may be processed according to traditional carbohydrate-concentration techniques, including thermal treatments.

As a first modification, a collected saliva sample can be concentrated using freeze concentration, or by a freeze-drying procedure similar to that reported by Daughters et al. First, a fresh sample is centrifuged at 4° C. and 1600×g for 15 min. The supernatant is transferred to a fresh 2 mL tube and the pellet discarded. The fresh cleared supernatant is then frozen for a 24 h period at −80° C. Considering that the solvent of the sample is mainly water, the concentration step resides in a lyophilization step to be performed overnight (from 12-16 h approximately considering the nature and volume of the sample). After freeze-drying, samples should be stored at −20° C. It has been determined that freeze-dried saliva samples under these conditions are stable for molecular studies up to 2 weeks. After these procedures, the samples could be subjected to AHG content analysis.

A second protocol for sample concentration could include evaporative concentration. After collection of a saliva sample, the sample could be centrifuged at 15,000×g and 30 min at 24° C. The supernatant would then be transferred to a fresh 2 mL tube and then subjected to concentration with a GeneVac EZ-2 plus at 30° C. for 2 h. A reduction of 10-15-fold in volume is achieved. Finally, concentrated samples are subjected to AHG content analysis. An alternative instrument that could be used in this approach is the Savant DNA 120 SpeedVac Concentrator (Thermo Electron Corporation).

In a third modification, a sample of saliva or urine, etc., is cleared of solids by centrifugation, then treated by addition of an equal volume of cool acetone or chloroform and held at 4° C. overnight 1 pse (12-16 h). Then, a centrifugation step at 15,000×g for 30 min at 4° C. is performed, the supernatant then removed and treated with a Savant DNA 120 SpeedVac Concentrator. The final sample is then analyzed.

A fourth method of sample pre-concentration is precipitation. Centrifugally-cleared saliva is mixed with 1 volume of an ammonium sulfate solution at 50% saturation. After a 10 min incubation period at room temperature, the sample is centrifuged at 15,000×g for 30 min at room temperature. The supernatant is discarded. After another cycle of ammonium sulfate+centrifugation step and discarding of the second supernatant, the final pellet is resuspended and subjected to analysis.

A fifth method of preconcentration is anion-exchange, metal chelate-affinity or hydrophobic interaction or reverse-phase adsorption, optionally using an internal-surface reverse phase or other access-controlled adsorbent. For anion-exchange adsorption of sugars, operation at high pH (>9) is preferred.

REFERENCES

The following references, to the extent that they provide exemplary procedural or other details supplementary to those set forth herein, are specifically incorporated herein by reference.

International Publication No. WO2008072702A1.

K Daughters, ASR Manstead, K Hubble, A Rees, A Thapar, SHM van Goozen. Salivary oxytocin concentrations in males following intrasanal administration of ocytoxin: A double-blind, cross-over study. PLOS ONE (2015).

R. J. Linhardt, H. G. Bazin, Separation and Purification of Carbohydrates, in: Glycosci. Chem. Chem. Biol., 2002: pp. 63-74.

R. A. Young, The Precipitation of Carbohydrates by Neutral Salts, J. Physiol. 22 (1898) 401-422.

The invention claimed is:

1. A method for analyzing a sample, the method comprising:
    (a) obtaining a sample comprising 1,5-anhydroglucitol and a first analyte;
    (b) adding glucose oxidase to the sample, wherein the glucose oxidase causes a first chemiluminescent reaction with the sample;
    (c) measuring photons from a first light response resulting from the first chemiluminescent reaction;
    (d) adding pyranose oxidase to the sample, wherein:
        the pyranose oxidase is sequentially added to the sample after glucose oxidase is added to the sample; and
        the pyranose oxidase causes a second chemiluminescent reaction with the sample;
    (e) measuring photons from a second light response resulting from the second chemiluminescent reaction; and
    (f) calculating a ratio of 1,5-anhydroglucitol and the first analyte based on the measured photons from the first light response to the photons from the second light response, wherein:
        measuring photons from the first light response resulting from the first chemiluminescent reaction and measuring photons from the second light response resulting from the second chemiluminescent reaction comprises measuring photons with a light detector; and
        comparing the photons from the first light response to the photons from the second light response to calculate a ratio of 1,5-anhydroglucitol and the first analyte comprises transmitting data to a computer processor.

2. The method of claim 1 wherein the sample comprises saliva.

3. The method of claim 1 wherein the sample comprises urine.

4. The method of claim 1 wherein the sample comprises blood.

5. The method of claim 1 wherein the sample comprises interstitial fluid.

6. The method of claim 1 wherein the first analyte is glucose, L-sorbose, D-xylose, D-galactose, glucono-δ-lactone, urea, creatinine, or creatine.

7. The method of claim 1 wherein the light detector is selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, and smart watch camera.

8. The method of claim 1 wherein the glucose oxidase and the pyranose oxidase are added to the sample via a microfluidic device.

9. The method of claim 1 further comprising accessing a lookup table with the computer processor.

10. The method of claim 9 wherein the lookup table comprises an indication of a physiological condition.

11. The method of claim 10 wherein the physiological condition is related to an insulin level of a person from whom the sample was obtained.

12. The method of claim 1 further comprising normalizing the ratio based on a measurement of a marker in the sample.

13. The method of claim 12 wherein the marker is urea, creatinine, creatine, human serum albumin, or hemoglobin.

14. The method of claim 13 wherein the sample comprises urine, blood or saliva.

* * * * *

UNITED STATES PATENT AND TRADEMARK OFFICE
CERTIFICATE OF CORRECTION

PATENT NO. : 11,307,146 B2
APPLICATION NO. : 15/661696
DATED : April 19, 2022
INVENTOR(S) : Richard C. Willson et al.

Page 1 of 1

It is certified that error appears in the above-identified patent and that said Letters Patent is hereby corrected as shown below:

In the Specification

Column 1, Line 11, please insert the following:
--STATEMENT REGARDING FEDERALLY FUNDED RESEARCH
This invention was made with government support under Grant No. 1449402-16-0011 awarded by the National Science Foundation. The government has certain rights in the invention.--

Signed and Sealed this
Twenty-seventh Day of February, 2024

Katherine Kelly Vidal
*Director of the United States Patent and Trademark Office*